US006403325B1

(12) United States Patent
Kosik et al.

(10) Patent No.: US 6,403,325 B1
(45) Date of Patent: Jun. 11, 2002

(54) METHODS AND COMPOUNDS FOR TREATING ALZHEIMER'S DISEASE

(75) Inventors: Kenneth S. Kosik, Belmont; Peter Morin, Needham, both of MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 09/107,112

(22) Filed: Jun. 30, 1998

Related U.S. Application Data

(60) Provisional application No. 60/051,359, filed on Jun. 30, 1997.

(51) Int. Cl.[7] .............................................. G01N 33/53
(52) U.S. Cl. ........................ 435/7.1; 435/7.2; 435/7.21; 435/7.8
(58) Field of Search ..................... 424/9.1, 9.2; 435/7.2, 435/7.21, 7.8, 7.1; 514/2, 12

(56) References Cited

FOREIGN PATENT DOCUMENTS

WO        WO 98/21315    *   5/1998

OTHER PUBLICATIONS

Cadigan et al., "Wnt Signaling: A Common Theme in Animal Development," *Genes & Development*, 11:3286–3305, 1997.
Leyns et al., "Frzb–1 is a Secreted Antagonist of Wnt Signaling Expressed in the Spemann Organizer," *Cell*, 88:747–756, Mar. 21, 1997.
Moon et al., "Structurally Related Receptors and Antagonists Compete for Secreted Wnt Ligands," *Cells*, 88:725–728, Mar. 21, 1997.
Sidow, "Diversification of the Wnt Gene Family on the Ancestral Lineage of Vertebrates," *Proc. Natl. Acad. Sci. USA*, 89:5098–5102, Jun., 1992.
Axelrod et al., "Interaction Between Wingless and Notch Signaling Pathways Mediated by Dishevelled," *Science*, 271:1826–1832, Mar., 1996.
Behrens et al., "Functional interaction of β–catenin with the transcription factor LEF–1," *Nature*, 382:638–642, Aug. 15, 1996.
Bhanot et al., "A new member of the frizzled family from Drosophila functions as a Wingless receptor," *Nature*, 382:225–230, Jul. 18, 1996.
Bradley et al., "A Soluble Form of Wnt–1 Protein with Mitogenic Activity on Mammary Epithelial Cells," *Molecular and Cellular Biology*, 15:4616–4622, Aug., 1995.

Couso et al., "Notch Is Required for wingless Signaling in the Epidermis of Drosophila," *Cell*, 79:259–272, Oct. 21, 1994.
Haass et al., "Amyloid β–peptide is produced by cultured cells during normal metabolism," *Nature*, 359:332–325, Sep. 24, 1992.
Houghten et al., "Generation and use of synthetic peptide combinatorial libraries for basic research and drug delivery," *Nature*, 354:84–86, Nov. 7, 1991.
Ingham, "Has the quest for a Wnt receptor finally frizzled out?" *Trends in Genetics*, 12:382–384, No. 10, Oct., 1996.
Lam et al., "A new type of synthetic peptide library for identifying ligand–binding activity," *Nature*, 354:82–84, Nov. 7, 1991.
Lin et al., "The cysteine–rich frizzled domain of Frzb–1 is required and sufficient for modulation of Wnt signaling," *Proceedings of the National Academy of Sciences*, 94:11196–11200, No. 21, Oct. 14, 1997.
Mayr et al., "Fritz: a secreted frizzled–related protein that inhibits Wnt activity," *Mechanisms of Development*, 63:109–125, 1997.
Roush, "Receptor for Vital Protein Finally Found," *Science*, 273:309, Jul. 19, 1996.
Wang et al., "A Large Family of Putative Transmembrane Receptors Homologous to the Product of the Drosophila Tissue Polarity Gene frizzled," *The Journal of Biological Chemistry*, 271:4468–4476, 1996.
Mus musculus putative transmembrane receptor (frizzled 4) mRNA, complete cds., Accession No. U43317, Feb. 24, 1996.
Human putative transmembrane receptor (frizzled 5) mRNA, complete cds., Accession No. U43318, Feb. 24, 1996.
Mus musculus putative transmembrane receptor (frizzled 7) mRNA, complete cds., Accession No. U43320, Feb. 24, 1996.
Mus musculus putative transmembrane receptor (frizzled 8) gene, complete cds., Accession No. U43321, Feb. 24, 1996.
Drosophila melangasre Dfz2 (Dfz2) gene, complete cds., Accession No. U65589, Sep. 1, 1996.
Human Fritz mRNA, complete cds., Accession No. U91903, Apr. 2, 1997.
Mesocricetus auratus Fritz (BHKriz) mRNA, partial cds., Apr. 2, 1997.

* cited by examiner

*Primary Examiner*—Marianne P. Allen
(74) *Attorney, Agent, or Firm*—Fish & Richardson P.C.

(57) ABSTRACT

Methods for identifying compounds which lower Aβ levels by acting through the Wnt signal transduction pathway are disclosed.

5 Claims, No Drawings

METHODS AND COMPOUNDS FOR TREATING ALZHEIMER'S DISEASE

REFERENCE TO RELATED APPLICATION

This application claims priority from provisional application No. 60/051,359, filed Jun. 30, 1997.

STATEMENT AS TO FEDERALLY SPONSORED RESEARCH

This invention was made with Government support under grant number AG06601, awarded by the National Institutes of Health. The Government has certain rights in the invention.

BACKGROUND OF THE INVENTION

This invention relates to methods and compounds for treating Alzheimer's disease.

Most current thinking about Alzheimer's disease suggests that the dementia characteristic of the disease results from aggregates formed in the brains of afflicted individuals. The aggregates are thought to be formed by a peptide of 40–43 amino acids called Aβ, which is derived from the amyloid precursor protein.

The Aβ peptide is normally found in trace amounts in blood and in cerebrospinal fluid. However, it can be found in increased levels in these fluids in patients suffering from some forms of Alzheimer's disease, and it is thought that increased concentrations of the Aβ peptide in these fluids contribute to its tendency to form aggregates. Because Alzheimer's disease can take many years to become clinically manifest, it is believed that over time even very small increases in circulating or cerebral spinal fluid Aβ levels may be damaging.

SUMMARY OF THE INVENTION

We have discovered that the addition of Wnt1 protein to Aβ peptide-producing cells affects the levels of Aβ peptide produced by these cells. Accordingly, the invention features methods of screening for compounds able to bind to the Wnt receptor and decrease the amount of Aβ peptide produced by these cells. The invention also features methods for treating Alzheimer's disease using compounds able to bind to the Wnt receptor and lower the amount of Aβ peptide produced.

In one aspect, the invention features a method of identifying a compound that inhibits expression of an Aβ peptide by contacting the compound with a Wnt receptor or a Wnt-binding fragment of Wnt receptor and determining the ability of the compound to bind to the Wnt receptor or Wnt-binding fragment of Wnt receptor. The binding of the compound is an indication that the compound lowers the level of Aβ peptide.

In one embodiment, the compound is a mammalian Wnt protein or a Wnt-receptor binding fragment of a mammalian Wnt protein, e.g., a human Wnt1 protein or a Wnt1-receptor binding fragment thereof. In another embodiment, the compound is a peptide mimetic of a Wnt protein. In yet another embodiment, the compound is a non-peptide mimetic of a Wnt protein.

In another aspect, the invention features a method of identifying a compound that inhibits expression of Aβ peptide by contacting a cell producing detectable levels of Aβ peptide with a Wnt antagonist and measuring the amount of Aβ peptide produced. A decrease in the amount of Aβ peptide produced by cell in the presence of the Wnt antagonist indicates that the Wnt antagonist is a compound that decreases Aβ peptide expression. The Wnt antagonist can include, e.g., a cysteine-rich domain (CRD)-containing fragment of the Wnt-receptor or the Fritz protein.

In another aspect, the invention features a method of identifying a compound that inhibits expression of Aβ peptide by (a) culturing a cell expressing a Wnt-receptor and Aβ peptide in the presence of the compound; and (b) evaluating the expression of Aβ peptide by the cell. A lowered level of Aβ peptide relative to a control cell indicates the compound inhibits expression of Aβ peptide.

In yet another aspect, the invention features a method of evaluating a compound for the ability to lower Aβ peptide levels in a mammal by contacting the compound with Wnt or a Wnt receptor-binding fragment of Wnt and Wnt-receptor or a Wnt binding fragment of Wnt receptor and determining the ability of the compound to enhance the binding of the Wnt or a Wnt receptor-binding fragment of Wnt with the Wnt receptor or a Wnt-binding fragment of Wnt receptor. An increase in the binding in the presence of the compound compared to the binding in the absence of the compound indicates that the compound lowers extracellular Aβ levels.

In a further aspect, the invention features a method for identifying candidate therapeutic agents for the treatment of Alzheimer's disease by (a) providing a cell which expresses a mammalian Wnt receptor, the cell comprising a reporter construct, the reporter construct comprising a sequence encoding a detectable protein, the sequence encoding the detectable protein being operably linked to a Wnt receptor responsive regulatory element; (b) contacting the cell with a test compound; (c) measuring the expression of the detectable protein in the presence of the test compound. An increase in the expression of the detectable protein in the presence of the test compound compared to the absence of the test compound indicates that the test compound is a candidate therapeutic agent for treatment of Alzheimer disease.

In one embodiment, the detectable protein is β-lactamase, chloramphenicol acetyltransferase (CAT), adenosine deaminase (ADA), aminoglycoside phosphotransferase (neo$^r$, G418$^r$), dihydrofolate reductase (DHFR), hygromycin-B-phosphotransferase (HPH), thymidine kinase (TK), lacZ (encoding β-galactosidase), or xanthine guaninephosphoribosyltransferase (XGPRT). The reporter gene can be alkaline phosphatase.

In another aspect, the invention features a method of inhibiting Aβ expression in a cell by identifying a Wnt-responsive cell that expresses Aβ peptide and contacting the cell with a compound that binds to Wnt, or to a Wnt receptor. The binding of the compound to Wnt inhibits Aβ expression by the cell.

The cell can be in a mammal, e.g., in vivo, or can be a cultured cell, i.e., in vitro. The compound can inhibit secretion of Aβ peptide from the cell, or can inhibit intracellular accumulation of Aβ from the cell.

Preferably, the Wnt protein is a Wnt1 protein.

In another aspect the invention features a method of inhibiting Aβ expression in a cell by identifying a Wnt-responsive cell that expresses Aβ peptide, and contacting the cell with a compound that binds to a Wnt receptor, wherein binding of the compound to the Wnt receptor inhibits Aβ expression by the cell.

In a further aspect, the invention features a method of treating Alzheimer's disease by introducing into a human suspected of needing treatment for Alzheimer's disease an effective amount of a compound binding to the human Wnt receptor. Binding of the compound is associated with decreased levels of Aβ polypeptide levels in the patient.

In a still further aspect, the invention features a method of preventing Alzheimer's disease by introducing into a human indicating as needing prophylactic treatment for Alzheimer's disease an effective amount of a compound characterized by binding to the human Wnt receptor.

In a further aspect, the invention features a method of lowering Aβ peptide levels in an mammal by administering a compound characterized by binding to a Wnt receptor in an amount sufficient to lower Aβ peptide levels.

An "Aβ peptide" includes an extracellular fragment of the β amyloid precursor protein that is 40–43 amino acids in length and is detected extracellularly.

A "Wnt protein" includes a member of the Wnt family of proteins.

A "Wnt receptor" includes a macromolecule, e.g., a protein, able to confer responsiveness to a Wnt ligand when expressed on the surface of a cell.

A "peptide mimetic" includes a Wnt analog in which one or more peptide bonds have been replaced with an alternative type of covalent bond which is not susceptible to cleavage by peptidases.

A "Wnt" antagonist is a compound that inhibits the activity of a Wnt protein.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

The present invention is based on the discovery that the Wnt protein, when added to cells that secrete Aβ peptide, affects the amount of Aβ peptide secreted by these cells.

The Wnt protein is a secreted protein encoded by a family of conserved genes that have been identified as both proto-oncogenes and as having functions important in development (reviewed in Nusse et al., Cell 69:1073, (1992)).

The Wnt protein is thought to act through cellular receptors encoded by members of the frizzled gene family. A receptor protein able to confer responsiveness to Wg, the homolog of Wnt in *Drosophila melanogaster*, is encoded by the frizzled2 locus ("Dfz2") (Bhanot et al., Nature 382:224 (1996); see also Roush, Science 273:309 (1996)). The full-length Dfz2 cDNA (SEQ ID NO:1) and amino acid sequence (SEQ ID NO:2) are shown in Table 1.

Dfz2 is a member of the frizzled ('fz) gene family, which is found in a wide variety of eukaryotes (Wang et al., J. Biol. Chem. 271:4468 (1996)). The Dfz2 gene has sequence features characteristic of this family: an amino terminal signal sequence precedes a domain characterized by ten invariant cysteine residues (the cysteine rich domain, or

TABLE 1

Nucleotide sequence (SEQ ID NO:1) and predicted
amino acid sequence (SEQ ID NO:2) of Dfz2
ACCESSION U65589

```
atgagacaca atcgactgaa ggtcctgatc ctgggactcg tcctcctgct gacatcttgt cgagcggatg gaccgctgca cagtgcggat cacggcatgg gcggaatggg catgggtggt cacggcctgg acgcgagtcc cgcacccggt tacggagtgc cagccatacc caaggatccc aatctgcgat gcgaggagat caccatacca atgtgtcggg gcattggcta caacatgaca tccttcccca acgaaatgaa ccatgagacc caggacgaag cgggcctgga ggtgcaccag ttctggcccc tggtggagat caaatgctcg ccggacctca agttcttcct gtgcagcatg tacacgccca tctgcctgga ggattaccac aagccgctgc ccgtttgccg gagtgtctgc gagagagccc gctcgggatg cgcacccatc atgcagcagt acagcttcga atggccggag agaatggcgt gcgagcactt gccccttcat ggtgacccg acaatctgtg catggaacag ccctcgtaca cggaggctgg cagcggtggc agctcgggcg gatcgggtgg ctctggcagc ggttccggct ccggcggcaa acggaagcaa ggaggcagtg gctcgggcgg cagtggggcc ggcggcagca gcggttccac ctcaacgaag ccgtgccgcg gacgcaattc aaaaaactgc caaaatcccc aaggagaaaa ggcaagcgga aaagagtgca gctgctcgtg ccgctcccca ctcatcttcc tggggaagga gcagctgctg cagcagcagt cgcagatgcc catgatgcac catccacacc actggtacat gaacctcact gtccaaagga tcgccggcgt tccaaactgc ggcataccgt gcaaggggcc cttcttcagc aacgacgaaa aggatttcgc cggcctctgg
```

TABLE 1-continued

Nucleotide sequence (SEQ ID NO:1) and predicted
amino acid sequence (SEQ ID NO:2) of Dfz2
ACCESSION U65589

```
atcgccctgt ggtcgggact gtgcttctgc agcacgctca tgaccctaac cacattcatc
atcgacaccg aaaggtttaa gtacccggag cggcccattg tcttcctctc cgcctgctac
ttcatggtgg cagtgggcta cctgtcgcgc aacttcctgc agaacgagga gatcgcctgc
gacggcctgc tgctccggga aagctccacg ggtccgcact cttgcaccct ggtcttcctg
ctcacctact tctttggcat ggcctcgtcc atctggtggg tgatcctcac tttcacctgg
ttcctggccg ctggtctgaa gtggggcaat gaggccatca ccaagcactc gcagtacttc
catctggccg cctggttgat tcccactgtc cagtccgtgg ccgtactcct gctctcggcg
gtggatggcg atcccattct gggcatctgc tatgtgggca acctcaatcc ggatcaccta
aagacctttg tgctggcccc gctcttcgtt tacctcgtaa tcggcaccac cttcctgatg
gccggctttg tgtccctctt ccgcatccgc tcggttatca agcaacaggg cggtgtagga
gctggtgtca aggcggacaa gctggagaaa ctgatgatca ggattggcat cttctcggtg
ctctacacgg tgccggccac catagttatc ggatgttacc tgtacgaagc agcctacttt
gaggactgga tcaaggccct ggcctgtcca tgcgcccagg tgaagggtcc cggcaagaag
cctctctact cggtcctgat gctcaagtac ttcatggccc tggccgtggg catcacctcg
ggcgtgtgga tctggtctgg caagacgctg gagagctggc gacgcttctg gcggagactc
ctaggagcgc cggaccgcac gggcgccaac caggcgctga tcaagcagcg gcctccgatc
ccgcatccct atgccggatc tggaatgggc atgcccgtgg gctcggcggc gggctccctg
ctggccacgc cctacaccca ggcgggcgga gcctcggtgg cctccaccag ccaccaccac
ctgcaccacc acgttctcaa gcagccggcg gccagccacg tatga MRHNRLKVLILGLVLLLTSCRADGPLHSADHGMGGMGMGGHGLDASPAPGYGVPAIPKDPNLRCEEITIPMCRGI
GYNMTSFPNEMNHETQDEAGLEVHQFWPLVEIKCSPDLKFFLCSMYTPICLEDYHKPLPVCRSVCERARSGCAPI
MQQYSFEWPERMACEHLPLHGDPDNLCMEQPSYTEAGSGGSSGGSGGSGSGSGGKRKQGGSGSGGSGAGGSSG
STSTKPCRGRNSKNCQNPQGEKASGKECSCSCRSPLIFLGKEQLLQQQSQMPMMHHPHHWYMNLTVQRIAGVPNC
GIPCKGPFFSNDEKDFAGLWIALWSGLCFCSTLMTLTTFIIDTERFKYPERPIVFLSACYFMVAVGYLSRNFLQN
EEIACDGLLLRESSTGPHSCTLVFLLTYFFGMASSIWWVILTFTWFLAAGLKWGNEAITKHSQYFHLAAWLIPTV
QSVAVLLLSAVDGDPILGICYVGNLNPDHLKTFVLAPLFVYLVIGTTFLMAGFVSLFRIRSVIKQQGGVGAGVKA
DKLEKLMIRIGIFSVLYTVPATIVIGCYLYEAAYFEDWIKALACPCAQVKGPGKKPLYSVLMLKYFMALAVGITS
GVWIWSGKTLESWRRFWRRLLGAPDRTGANQALIKQRPPIPHPYAGSGMGMPVGSAAGSLLATPYTQAGGASVAS
TSHHHLHHHVLKQPAASHV
```

"CRD"). The CRD is followed by a highly divergent region of 40–100 mainly hydrophilic residues encoding seven putative membrane-spanning segments (Bhanot et al.).

The present invention provides methods of screening for compounds that are able lower the levels of Aβ peptide by acting via the Wnt-receptor protein, and for methods of treating Alzheimer's disease using these compounds. One way to identify compounds able to lower Aβ peptide levels is based on the interaction of the compound with the Wnt receptor, and/or compounds which activate other members of the Wnt signal transduction pathway.

Methods of Screening for Wnt-Receptor Binding Compounds Able To Lower Aβ Levels

Compounds able to lower levels of Aβ peptide can be identified based on their interaction with a Wnt receptor or a Wnt-binding fragment of a Wnt receptor.

Screening assays can be performed with a Wnt receptor, or a Wnt-binding fragment of a Wnt receptor. The Wnt receptor protein can be a member of the frizzled protein family, such as those described in Barnot et al., above. The screening assays can also be performed using the mammalian frizzled sequences Hfz5 (human), mouse Mfz4, Mfz7, or Mfz8 (mouse), or on cells expressing frizzled sequences. The nucleic acid sequences and predicted amino acid sequences of Hfz5, Mfz4, Mfz7, or Mfz8 are shown in Tables 2–5.

When the Wnt receptor is a frizzled protein, a Wnt-binding fragment of the receptor can include the CRD domain of a frizzled protein, e.g., the fragments summarized in FIG. 2 of Mayr et al., Mech. Dev. 63:109–125, 1997.

These fragments include amino acids 1–264 (SEQ ID NO:15) of the human Hfz5 amino acid sequence shown in Table 2.

The Wnt receptor can alternatively be a member of the Notch family of proteins. Genetic and biochemical

TABLE 2

Nucleotide sequence (SEQ ID NO:3) and predicted
amino acid (SEQ ID NO:4) sequence of Hfz5
ACCESSION U43318

| | | | | | |
|---|---|---|---|---|---|
| acccagggac | ggaggaccca | ggctggcttg | gggactgtct | gctcttctcg | gcgggagccg |
| tggagagtcc | tttccctgga | atccgagccc | taaccgtctc | tccccagccc | tatccggcga |
| ggagcggagc | gctgccagcg | gaggcagcgc | cttcccgaag | cagtttatct | ttggacggtt |
| ttctttaaag | gaaaaacgaa | ccaacaggtt | gccagccccg | gcgccacaca | cgagacgccg |
| gagggagaag | ccccggcccg | gattcctctg | cctgtgtgcg | tccctcgcgg | gctgctggag |
| gcgagggag | ggaggggggcg | atggctcggc | ctgacccatc | cgcgccgccc | tcgctgttgc |
| tgctgctcct | ggcgcagctg | gtgggccggg | cggccgccgc | gtccaaggcc | ccggtgtgcc |
| aggaaatcac | ggtgcccatg | tgccgcggca | tcggctacaa | cctgacgcac | atgcccaacc |
| agttcaacca | cgacacgcag | gacgaggcgg | gcctggaggt | gcaccagttc | tggccgctgg |
| tggagatcca | atgctcgccg | gacctgcgct | tcttcctatg | cactatgtac | acgcccatct |
| gtctgcccga | ctaccacaag | ccgctgccgc | cctgccgctc | ggtgtgcgag | cgcgccaagg |
| ccggctgctc | gccgctgatg | cgccagtacg | gcttcgcctg | gcccgagcgc | atgagctgcg |
| accgcctccc | ggtgctgggc | cgcgacgccg | aggtcctctg | catggattac | aaccgcagcg |
| aggccaccac | ggcgcccccc | aggcctttcc | cagccaagcc | caccctttcca | ggcccgccag |
| gggcgccggc | ctcgggggc | gaatgccccg | ctgggggccc | gttcgtgtgc | aagtgtcgcg |
| agcccttcgt | gcccattctg | aaggagtcac | acccgctcta | caacaaggtg | cggacgggcc |
| aggtgcccaa | ctgcgcggta | ccctgctacc | agccgtcctt | cagtgccgac | gagcgcacgt |
| tcgccaccttt | ctggataggc | ctgtggtcgg | tgctgtgctt | catctccacg | tccaccacag |
| tggccaccttt | cctcatcgac | atggacacgt | tccgctatcc | tgagcgcccc | atcatcttcc |
| tgtcagcctg | ctacctgtgc | gtgtcgctgg | gcttcctggt | gcgtctggtc | gtgggccatg |
| ccagcgtggc | ctgcagccgc | gagcacaacc | acatccacta | cgagaccacg | ggccctgcac |
| tgtgcaccat | cgtcttcctc | ctggtctact | tcttcggcat | ggccagctcc | atctggtggg |
| tcatcctgtc | gctcacctgg | ttcctggccg | ccgcgatgaa | gtgggcaac | gaggccatcg |
| cgggctacgg | ccagtacttc | cacctggctg | cgtggctcat | ccccagcgtc | aagtccatca |
| cggcactggc | gctgagctcc | gtggacgggg | acccagtggc | cggcatctgc | tacgtgggca |
| accagaacct | gaactcgctg | cggcgcttcg | tgctgggccc | gctggtgctc | tacctgctgg |
| tgggcacgct | cttcctgctg | gcgggcttcg | tgtcgctctt | ccgcatccgc | agcgtcatca |
| agcaggcgg | caccaagacg | gacaagctgg | agaagctcat | gatccgcatc | ggcatcttca |
| cgctgctcta | cacggtcccc | gccagcattg | tggtggcctg | ctacctgtac | gagcagcact |
| accgcgagag | ctgggaggcg | gcgctcacct | gcgcctgccc | gggccacgac | accggccagc |
| cgcgcgccaa | gcccgagtac | tgggtgctca | tgctcaagta | cttcatgtgc | ctggtggtgg |
| gcatcacgtc | gggcgtctgg | atctggtcgg | gcaagacggt | ggagtcgtgg | cggcgtttca |
| ccagccgctg | ctgctgccgc | ccgcggcgcg | gccacaagag | cggggcgcc | atggccgcag |
| gggactaccc | cgaggcgagc | gccgcgctca | caggcaggac | cgggccgccg | ggccccgccg |

TABLE 2-continued

Nucleotide sequence (SEQ ID NO:3) and predicted
amino acid (SEQ ID NO:4) sequence of Hfz5
ACCESSION U43318 ccacctacca caagcaggtg tccctgtcgc acgtgtagga ggctgccgcc gagggactcg gccggagagc tgaggggagg ggggcgtttt gtttggtagt tttgccaagg tcacttccgt ttaccttcat ggtgctgttg ccccctcccg cggcgacttg gagagaggga agaggggcgt tttcgaggaa gaacctgtcc caggtcttct ccaagggggcc cagctcacgt gtattctatt ttgcgtttct tacctgcctt ctttatggga accctctttt taatttatat gtat

MARPDPSAPPSLLLLLLAQLVGRAAAASKAPVCQEITVPMCRGIGYNLTHMPNQFNHDTQDEAGLEVHQFWPLVE

IQCSPDLRFFLCTMYTPICLPDYHKPLPPCRSVCERAKAGCSPLMRQYGFAWPERMSCDRLPVLGRDAEVLCMDY

NRSEATTAPPRPFPAKPTLPGPPGAPASGGECPAGGPFVCKCREPFVPILKESHPLYNKVRTGQVPNCAVPCYQP

SFSADERTFATFWIGLWSVLCFISTSTTVATFLIDMDTFRYPERPIIFLSACYLCVSLGFLVRLVVGHASVACSR

EHNHIHYETTGPALCTIVFLLVYFFGMASSIWWVILSLTWFLAAAMKWGNEAIAGYGQYFHLAAWLIPSVKSITA

LALSSVDGDPVAGICYVGNQNLNSLRRFVLGPLVLYLLVGTLFLLAGFVSLFRIRSVIKQGGTKTDKLEKLMIRI

GIFTLLYTVPASIVVACYLYEQHYRESWEAALTCACPGHDTGQPRAKPEYWVLMLKYFMCLVVGITSGVWIWSGK

TVESWRRFTSRCCCRPRRGHKgGGAMAAGDYPEASAALTGRTGPPGPAATYHKQVSLSHV

TABLE 3

Nucleotide sequence (SEQ ID NO:5) and predicted
amino acid sequence (SEQ ID NO:6) of Mfz4
ACCESSION U43317 tcgacctcaa cacaaagacc tgggtcgtga gacacacgcg tagagtcagg cggcttcccc gaaaaccgga ctcggccggc gccgagtctg ggtccccgcc ttcaaccatg accctagcaa tccatccctc ggcccgggct ccggacgtct gatattccgc acattctcgt acaactgctg gagaggcgac tgctgccccc ttgtcgccct tggcgcctta ccgcattccc tatccggagt tgggagcagc gcggccaccg gcgcccctgt gcaaactggg ggtgtctgct agatcagcct ctgccgctgc tgcccgcagc tctggccatg gcctggccgg gcacagggcc gagcagccgg ggggcgcctg gaggcgtcgg gctcaggctg gggctgctgc tgcagttcct cctgctcctg cggccgacac tggggttcgg ggacgaggag gagcggcgct gcgacccccat ccgcatcgcc atgtgccaga acctcggcta caacgtgacc aagatgccca acttagtggg acacgagctg cagacagacg ccgagctgca gctgacaact ttcacgccgc tcatccagta cggctgctcc agccagctgc agttcttcct ttgttcggtt tatgtgccaa tgtgcacaga aagatcaac atccccatcg gccgtgcgg tggcatgtgc ctttcagtca agagacgctg tgaaccagtc ctgagagaat ttgggtttgc ctggcccgac accctgaact gcagcaagtt cccgccccag aacgaccaca accacatgtg catggaagga ccaggtgatg aagaggttcc cttgccccac aagactccca tccagcccgg ggaagagtgc cactccgtgg gaagcaattc tgatcagtac atctgggtga agaggagcct gaactgtgtt ctcaagtgtg gctacgatgc tggcttgtac agccgctcag ctaaggagtt cacgatatt tggatggctg tgtgggccag cctctgcttc atctccacca ccttcaccgt gctgacctttc ctgattgatt catccaggtt ttcttaccct gagcgcccca tcatatttct cagtatgtgc tataatattt atagcattgc ttatattgtt cggctgactg taggccggga aaggatatcc tgtgattttg aagaggcggc agagcccgtt TABLE 3-continued Nucleotide sequence (SEQ ID NO:5) and predicted
amino acid sequence (SEQ ID NO:6) of Mfz4
ACCESSION U43317 ctcatccaag aaggacttaa gaacacagga tgtgcaataa ttttcttgct gatgtacttt tttggaatgg ccagctccat ttggtgggtt attctgacac tcacttggtt tttggcagcc ggactcaagt ggggtcatga agccattgaa atgcacagtt cttatttcca catcgcagcc tgggctattc ccgcagtgaa aaccattgtc atcttgatta tgagactagt ggatgccgat gaactgactg gcttgtgcta tgttgggaac caaaacctag atgccctcac tggctttgtg gtggctcctc tctttacgta tttggtgatt ggaacgctgt tcattgcggc gggtttggtg gccttattca aaattcggtc caatcttcaa aaagacggga caaagacaga caagttggaa aggctaatgg tcaagatcgg ggtcttctca gtactgtaca cggttcctgc aacctgtgtg attgcctgtt atttctatga aatctcaaac tgggcactct ttcgatattc tgcagatgac tcaaacatgg cagttgaaat gttgaaaatt tttatgtctt tgctcgtggg catcacttca ggcatgtgga tttggtctgc caaaactctt cacacgtggc aaaagtgttc taaccgattg gtgaattctg ggaaggtaaa gagagagaag aggggaatg gttgggtgaa gccaggaaaa ggcaacgaga ctgtggtata agactagccg gcttcctcgt tcctcattgt gaaggaagtg atgcagggaa tctcagtttg aacaaactta gaaacacttc agcccacaca cacccacgtc agcccaccac cactcaccca actcagcatc agaagaccaa tggcttcact gcagactttg gaatggtcca aaatggaaaa gccagttaag aggttttcaa agctgtgaaa atcaaaatg ttgatcactt tagcaggtca cagcttggag tccgtggagg tcccgcctag attcctgaag cccagggtga tagtgtttgc tcctactggg tgggatttca actgtgagtt gataacatgc aaggagaaag attaattttt aaaacccttt taaatttaa atagtaacta aggtcttgca gatagcaaag tgatctataa acactggaaa tgctgggttg ggagacgtgt tgcagagttt ttatatngtt tnnctggtct aacataaaca tcttctggcc tacactgtct gctgtttaga actctgtagc gcactcccag aggtggtgtc aaaatccttc agtgccttgt cgtaaaacag aattgtttga gcaaacaaaa gtactgtact aacacacgta aggtatccag tggatttctc tctcctgaaa tttcaacatc cctaattcta ggcagcccct gttttcttca ctttaaacta atgactcaaa aaaaaaaagg ttatttttat aggattttt tttgcactgc agcatgccta atgagaggaa aaggaggtga tcacttctga caatcactta attcagagaa aaatgagatt tgctaattga cttaccttcc gaccoctaga gaccctattg cattaagcaa tgtttaagca attggggact t

MAWPGTGPSSRGAPGGVGLRLGLLLQFLLLLRPTLGFGDEEERRCDPIRIAMCQNLGYNVTKMPNLVGHELQTDA

ELQLTTFTPLIQYGCSSQLQFFLCSVYVPMCTEKINIPIGPCGGMCLSVKRRCEPVLREFGFAWPDTLNCSKFPP

QNDHNHMCMEGPGDEEVPLPHKTPIQPGEECHSVGSNSDQYIWVKRSLNCVLKCGYDAGLYSRSAKEFTDIWMAV

WASLCFISTTFTVLTFLIDSSRFSYPERPIIFLSMCYNIYSIAYIVRLTVGRERISCDFEEAAEPVLIQEGLKNT

GCAIIFLLMYFFGMASSIWWVILTLTWFLAAGLKWGHEAIEMHSSYFHIAAWAIPAVKTIVILIMRLVDADELTG

LCYVGNQNLDALTGFVVAPLFTYLVIGTLFIAAGLVALFKIRSNLQKDGTKTDKLERLMVKIGVFSVLYTVPATC

VIACYFYEISNWALFRYSADDSNMAVEMLKIFMSLLVGITSGMWIWSAKTLHTWQKCSNRLVNSGKVKREKRGNG

WVKPGKGNETVV

TABLE 4

Nucleotide sequence (SEQ ID NO:7) and predicted
amino acid sequence (SEQ ID NO:8) of Mfz7
ACCESSION U43320

```
tttgaaggta accggagaag cttgttgctc gtcgccgcag agaaagccgc accgttacgt
ctcggngggg agggtaaggc gacacccctt ccctcgtacc cccactccag gcccaggagt
ttgaactccg gcggctgcgt gagtgccacg tggaggcggc tgcggcgccc ctcggctggc
ggcctcgccc ccgctgtgca ggcaccctag caccctcggc tccgcgccgc ccacggcggc
cccggcgccg ggaggactct catgcgccgg ccgggcggcg gcgcctccct gtatccaagc
ctctccccag cgcctcgtct ttttcctcca gctgagaacg ccgctgcact cgcgaccggc
gatgcgggc cccggcacgg cggcgtcgca ctcgcccctg ggcctctgcg ccctggtgct
tgctcttctg ggcgcgctgc ccacggacac ccgggctcag ccatatcacg gcgagaaagg
catctcggta ccggaccacg gcttctgcca gcccatctcc atcccgttgt gcacggatat
cgcctacaac cagaccatcc tgcccaacct gctgggccac acgaaccaag aggacgcggg
cctcgaggtg caccagttct accctctggt aaaggtgcag tgttctcctg agctacgctt
cttcttatgc tctatgtacg cacccgtgtg caccgtgctc gaccaagcca ttcctccgtg
ccgttccttg tgcgagcgcg cccgacaggg ctgcgaggcg ctcatgaaca agttcggctt
ccagtggcca gagcggttgc gctgcgagaa cttcccagtg cacggtgccg gcgagatctg
cgtggggcag aacacgtccg acggctccgg gggcgcgggc ggcagtccca ccgcctaccc
tactgctccc tacctgccag acccacctttt cactgcgatg tccccctcag atggcagagg
ccgcttgtct ttcccttct cgtgtccgcg ccagctcaag gtgcccccct acctgggcta
ccgcttccta ggtgagcgtg actgcggtgc cccgtgtgag ccgggccgtg ctaacggcct
catgtacttt aaagaagagg agagacggtt cgcccgcctc tgggtgggtg tgtggtcagt
gctgtcgtgc gcctcgacgc tcttcacggt gctcacctac ctagtggaca tgcgtcgctt
cagctatcca gagcgaccca tcatcttcct gtcgggttgc tacttcatgg tggcagtggc
gcacgtggca ggcttcctgc tagaggaccg tgccgtgtgc gtggagcgct ctcggacga
tggctaccgc acggtggcgc agggcaccaa gaaggagggc tgcaccatcc tcttcatggt
gctttacttc ttcggtatgg ccagctccat ctggtgggtc attctgtccc tcacttggtt
cctggcagct ggcatgaagt ggggccacga ggccatcgag gccaactcgc agtactttca
tctgccgcg tgggctgtgc cagcggtcaa gacaatcacc attttggcca tgggccaggt
ggatggtgac ctactcagtg gagtgtgcta cgtgggcctg tctagtgtgg atgcattgcg
gggcttcgtg ctggcgccct tgttcgtcta cctcttcatc gggacgtcct tcctgttggc
cggctttgtg tctctctttc gcatccgcac catcatgaag cacgacggca ccaagacaga
gaagctggag aagctgatgg tgcgcatcgg cgtcttcagc gtgctctaca cggtgccggc
caccatcgtg ttggcctgct actttatga gcaggccttc cgagagcact gggaacgcac
ctggctcctg cagacttgca agagctacgc tgtgccctgc cctccgcgcc acttctctcc
catgagcccc gactttacag tcttcatgat caagtacctg atgaccatga tcgtgggcat
cactacgggc ttctggatct ggtcgggcaa gaccctgcag tcatggcgtc gcttctacca
cagactcagc cacagcagca agggggaaac tgcggtatga gccccggtcc ttacccaccc
ttgcctcttc tacccttta caggaggaga ggcatggtag ggagagaact gctgggtggg
ggcttgtttc cgtaagctac ctgcccccctc cactgagctt taacctggaa gtgagaagtt
atttggaggt gagaagagat ttgggggcga gagatggttt
```

TABLE 4-continued

Nucleotide sequence (SEQ ID NO:7) and predicted amino acid sequence (SEQ ID NO:8) of Mfz7
ACCESSION U43320

MRGPGTAASHSPLGLCALVLALLGALPTDTRAQPYHGEKGISVPDHGFCQPISIPLCTDIAYNQTILPNLLGHTN

QEDAGLEVHQFYPLVKVQCSPELRFFLCSMYAPVCTVLDQAIPPCRSLCERARQGCEALMNKFGFQWPERLRCEN

FPVHGAGEICVGQNTSDGSGGAGGSPTAYPTAPYLPDPPFTAMSPSDGRGRLSFPFSCPRQLKVPPYLGYRFLGE

RDCGAPCEPGRANGLMYFKEEERRFARLWVGVWSVLSCASTLFTVLTYLVDMRRFSYPERPIIFLSGCYFMVAVA

HVAGFLLEDRAVCVERFSDDGYRTVAQGTKKEGCTILFMVLYFFGMASSIWWVILSLTWFLAAGMKWGHEAIEAN

SQYFHLAAWAVPAVKTITILAMGQVDGDLLSGVCYVGLSSVDALRGFVLAPLFVYLFIGTSFLLAGFVSLFRIRT

IMKHDGTKTEKLEKLMVRIGVFSVLYTVPATIVLACYFYEQAFREHWERTWLLQTCKSYAVPCPPRHFSPMSPDF

TVFMIKYLMTMIVGITTGFWIWSGKTLQSWRRFYHRLSHSSKGETAV

TABLE 5

Nucleotide sequence (SEQ ID NO:9) and predicted amino acid sequence (SEQ ID NO:10) of Mfz8
ACCESSION U43321 gggggagggc cggacgactc cagcctaggt ttccaaccct gctgcctgaa aaggagatag actgttgcta ttctcctctg cagagaaaag tgggacacga cccgctctcc cttttctcag attcctcact gcagagccct cctgcgcgcc gcctagagaa ggaggacttg gggtcccagc gcgcagcatg gagtggggtt acctgttgga agtgacctcg ctcctagccg ccttggcggt gctacagcgc tctagcggcg ctgccgcggc ttcggccaag gagctggcgt gccaagagat cacggtgccg ttgtgcaaag gcatcggtta caactacact tacatgccca accagttcaa ccacgacacg caagatgagg cgggcctaga ggtgcaccag ttttggccgc tggtggagat acagtgctcc ccggacctca agttcttcct gtgtagcatg tacacgccca tctgcctgga ggactacaag aagcctctgc cgccttgtcg ctctgtgtgt gaacgcgcca aggccggctg cgcgccgctc atgcgccagt acggctttgc ttggcctgac cgcatgcgct gcgatcggtt gccggagcag ggcaacccgg acactctgtg catggactac aaccgcaccg acctcaccac ggccgcgccc agcccaccgc gccgcctgcc tccgccgcct cctcccggcg agcagccgcc ctctggcagc ggccacagcc gcccgccagg ggccaggccc ccacatcgtg gcggcagcag tagggcagc ggggacgcgg cggctgcgcc cccttcgcgc ggcgggaagg cgaggccccc tggtggcggc gctgctccct gcgagccggg gtgccagtgc cgcgcgccca tggtgagcgt gtccagcgaa cgccacccgc tctacaaccg cgtcaagacc ggccagatcg ccaactgtgc gctgccctgc cacaacccct tctttagcca ggatgagcgc gccttcaccg tcttctggat cggcctgtgg tcggtgctct gcttcgtctc caccttcgcc actgtctcta ccttcctcat cgatatggag cgctttaagt acccggaacg gcccatcata ttcctctccg cctgttacct cttcgtgtct gtcgggtacc tggtgcgcct ggtggcagga catgagaaag tggcctgcag cggcggcgct ccgggtgctg gcggacgtgg gggtgcgggc ggcgcggcgg cggctggcgc aggggcagcg ggacgggggg cgagcagccc gggcgcgcgc ggcgagtacg aggagctggg cgcagttgag cagcatgttc gctatgagac cactggcccc gcgctgtgca cggtggtctt tctccttgtc tactttttg gcatggccag ctccatctgg tgggtaatcc tgtcgctcac gtggttcttg gcagctggca tgaagtgggg taacgaggcc atagcaggct actcgcagta

TABLE 5-continued

Nucleotide sequence (SEQ ID NO:9) and predicted
amino acid sequence (SEQ ID NO:10) of Mfz8
ACCESSION U43321

```
cttccacctg gccgcgtggc ttgtgcccag cgtcaagtcc atcgcggtgc tggcgctcag ctccgtagac ggcgacccgg tggcgggcat ctgctacgtg ggcaaccaga gccttgacaa cctacgcggc tttgtgctgg cgccactggt tatctacctc ttcattggga ctatgtttct gttagctggc ttcgtgtcgc tgttccgaat ccgttcagtc atcaagcagc aaggaggtcc aactaagaca cacaagctag aaaaactcat gatccgcttg ggcctcttca ccgtgctcta cacggtgccc gctgccgtcg ttgtcgcctg cctttctat gagcagcaca accgaccgcg ctgggaggcc acgcacaact gcccatgcct tcgggacctg caaccggacc aggctcgcag gcccgattac gcggtcttca tgctcaagta cttcatgtgc ctagtagtgg gcatcacatc gggcgtgtgg gtctggtccg gcaagactct ggagtcctgg cgcgcgttgt gcactaggtg ctgctgggcc agcaagggcg ctgcagtagg cgcgggcgct ggaggcagcg gccctggggg cagtggaccc gggcccggcg gaggtgggg acacggcgga ggcgggggat ccctctacag cgacgtcagt accggcctga cgtggcggtc tggcacggcc agctctgtat cttaccctaa gcaaatgcca ttgtcccagg tctgaaccct acgtggatgc ccagaagggg cggagaggag tggggatgg ggaacccgtg ggcggcgaag ggaccccaga ccggccaggg ttcccacccc ttcccagtgt tgactgctat agcatgacaa tgaagtgtta atggtatcca ttagcagcgg ggacttaaat gactccctta g
```

MEWGYLLEVTSLLAALAVLQRSSGAAAASAKELACQEITVPLCKGIGYNYTYMPNQFNHDTQDEAGLEVHQFWPL

VEIQCSPDLKFFLCSMYTPICLEDYKKPLPPCRSVCERAKAGCAPLMRQYGFAWPDRMRCDRLPEQGNPDTLCMD

YNRTDLTTAAPSPPRRLPPPPPPGEQPPSGSGHSRPPGARPPHRGGSSRGSGDAAAAPPSRGGKARPPGGGAAPC

EPGCQCRAPMVSVSSERHPLYNRVKTGQIANCALPCHNPFFSQDERAFTVFWIGLWSVLCFVSTFATVSTFLIDM

ERFKYPERPIIFLSACYLFVSVGYLVRLVAGHEKVACSGGAPGAGGRGGAGGAAAAGAGAAGRGASSPGARGEYE

ELGAVEQHVRYETTGPALCTVVFLLVYFFGMASSIWWVILSLTWFLAAGMKWGNEAIAGYSQYFHLAAWLVPSVK

SIAVLALSSVDGDPVAGICYVGNQSLDNLRGFVLAPLVIYLFIGTMFLLAGFVSLFRIRSVIKQQGGPTKTHKLE

KLMIRLGLFTVLYTVPAAVVVAC/
LFYEQHNRPRWEATHNCPCLRDLQPDQARRPDYAVFMLKYFMCLVVGITSGV

WoVWSGKTLESWRALCTRCCWASKGAAVGAGAGGSGPGGSGPGPGGGGHGGGGGSLYSDVSTGLTWRSGTASSVS

YPKQMPLSQV

--- studies have implicated products of the Notch locus as being involved in the reception of Wnt signals (Couso et al., Cell 79:259 (1994); Axelrod et al., Science 271:1826 (1996). When Notch family members are used, calcium may be added in the medium to facilitate binding (Ingham, Trends Genet. 12:382, 384 (1996)).

One way the Wnt receptor protein can be provided is on a cell responsive to Wnt. Several such cell lines are known, e.g., PC12 pheochromocytoma cells and C57MG mammary carcinoma cells.

Alternatively, the Wnt receptor can be introduced into a cell that is otherwise not responsive to Wnt using methods known in the art, e.g., as a polypeptide or by introducing cDNA encoding a Wnt receptor into an appropriate cell. Thus, the source of Wnt-responsive cell is not critical when compounds are screened using cell-based assays. For example, Barnot et al., supra, have demonstrated that the Dfz2 protein confers Wg-responsiveness on Drosophila S2 cells and human embryonic kidney cells.

Candidate compounds can be screened for binding to the Wnt receptor using methods known in the art. Binding may be assessed by examining compounds for the ability to stimulate the Wnt signal transduction pathway, e.g., by assessing stabilization of proteins in the β-catenin family as is described in Bahnot et al. for the armadillo (Arm) protein. Another way in which Wnt activity can be assessed by measuring activation of the T cell factor lymphoid enhancer factor (TcF-Lef) (Behrens et al., Nature 382:638–42, 1996).

In some situations it may be desirable to first screen candidate compounds for direct binding to the Wnt receptor, or Wnt-binding fragments thereof, such as the CRD domain, in vitro, e.g., in a gel mobility shift assay and/or an immunoprecipitation assay, and then test Wnt-receptor binding proteins for the ability to lower Aβ levels in a subsequent step.

Levels of Aβ peptide can be measured using methods well-known in the art, e.g., the methods described in Haass et al., Nature 359:322–25, (1992).

The assays described herein are designed to identify compounds that interact with (e.g., bind to) a Wnt receptor. These compounds can include, but are not limited to, those that interact with members of the frizzled family, These compounds can also include those that interact with (e.g., bind to) intracellular proteins that interact with Wnt (including, but not limited to, the Wnt receptor) compounds that interfere with the interaction of Wnt with transmembrane or intracellular proteins involved in Wnt-mediated signal transduction, e.g., proteins analogous to the dishelved and Arm gene products, and to compounds that modulate the activity of a Wnt receptor gene (i.e., modulate the level of Wnt receptor gene expression). Assays can additionally be utilized which identify compounds that bind to Wnt receptor gene regulatory sequences (e.g., promoter sequences) and which may modulate Wnt receptor gene expression.

The compounds can also be those resembling, e.g., having homology to, the Wnt receptor, or fragments thereof, e.g., fragments containing the CRD-domain. Some examples of CRD domain-containing polypeptides are amino acids 1–348 (SEQ ID NO:16) of the Df2z homolog (SEQ ID NO:2) and amino acids 1–264 (SEQ ID NO:15) of the human Hfz5 homolog. An example of a compound of this type is the human Fritz protein (SEQ ID NO:14), which is a secreted protein having homology to the CRD-domain found in members of the frizzled family, and which has been reported to antagonize Wnt function (Lin et al., Proc. Natl. Acad. Sci. (USA) 94:11196–11200 (1997); Mayr et al., Mec. Dev. 63: 109–25 (1997)). Nucleic acids encoding human and mouse Fritz sequences, and the predicted amino acid sequences encoded by these sequences, are shown in Tables 6 and 7, respectively.

In general, compounds that can be screened in accordance with the invention include, but are not limited to polypeptides, peptides, antibodies and fragments thereof, and other organic compounds (e.g., peptidomimetics) that bind to the extra-cellular domain or cysteine-rich domain of a Wnt receptor and either mimic the activity triggered by the natural ligand (i.e., agonists) or inhibit the activity triggered by the natural ligand (i.e., antagonists); as well as peptides, antibodies or fragments thereof, and other organic compounds that binding to Wnt.

Such compounds can include, but are not limited to, peptides such as, for example, soluble peptides, including but not limited to members of random peptide libraries; (see, e.g., Lam, et al., *Nature* 354:82–84, 1991; Houghten, et al., *Nature* 354:84–86, 1991), and combinatorial chemistry-derived molecular library made of D- and/or L-configuration amino acids, phosphopeptides (including, but not limited to, members of random or partially degenerate, directed phosphopeptide libraries; see, e.g., Songyang, Z. et al., 1993, *Cell* limited to, polyclonal, monoclonal, humanized, anti-idiotypic, chimeric or single chain antibodies, and Fab, F(ab')2 and Fab expression library fragments, and epitope-binding fragments thereof), and small organic or inorganic molecules.

Other compounds that can be screened in accordance with the invention include but are not limited to small organic molecules that are able to cross the blood-brain

TABLE 6

Nucleotide sequence (SEQ ID NO:11) and predicted ainino acid sequence (SEQ ID NO:12) of hfiz
ACCESSION U91903

```
cggagacggc ggagcgggcc ttgttggcgt ccactgcgcg gntgcaccct gccccatcct gccgggatca tggtctgcgg cagcccggga gggatgctgc tgctgcgggc cgggctgctt gccctggctg ctctctgcct gctccgggtg cccggggctc gggctgcagc ctgtgagccc gtccgcatcc ccctgtgcaa gtccctgccc tggaacatga ctaagatgcc caaccacctg caccacagca ctcaggacaa cgccatcctg gccatcgagc agttcgaagg tctgctgggc acccactgca gccccgatct gctcttcttc ctctgtgcca tgtacgcgcc catctgcacc attgacttcc agcacgagcc catcaagccc tgtaagtctg tgtgcgagcg ggcccggcag ggctgtgagc ccatactcat caagtaccgc cactcgtggc cggagaacct ggcctgcgag gagctgccag tgtacgacag gggcgtgtgc atctctcccg aggccatcgt tactgcggac ggagctgatt ttcctatgga ttctagtaac ggaaactgta gaggggcaag cagtgaacgc tgtaaatgta agcctattag agctacacag aagacctatt tccggaacaa ttacaactat gtcattcggg ctaaagttaa agagataaag actaagtgcc atgatgtgac tgcagtagtg gaggtgaagg agattctaaa gtcctctctg gtaaacattc cacgggacac tgtcaacctc tataccagct ctggctgcct ctgccctcca cttaatgtta atgaggaata tatcatcatg ggctatgaag atgaggaacg ttccagatta ctcttggtgg aaggctctat agctgagaag tggaaggatc gactcggtaa aaaagttaag cgctgggata tgaagcttcg tcatcttgga ctcagtaaaa gtgattctag caatagtgat tccactcaga gtcagaagtc tggcaggaac tcgaaccccc ggcaagcacg caactaaatc ccgaaataca aaaagtaaca cagtggactt
```

TABLE 6-continued

Nucleotide sequence (SEQ ID NO:11) and predicted
amino acid sequence (SEQ ID NO:12) of hfiz
ACCESSION U91903 cctattaaga cttacttgca ttgctggact agcaaaggaa aattgcacta ttgcacatca tattctattg tttactataa aaatcatgtg ataactgatt attacttctg tttctctttt ggtttctgct tctctcttct ctcaacccct ttgtaatggt ttgggggcag actcttaagt atattgtgag ttttctattt cactaatcat gagaaaaact gttcttttgc aataataata aattaaacat gctgttacca gagcctcttt gctggagtct ccagatgtta atttactttc tgcaccccaa ttgggaatgc aatattggat gaaagagag gtttctggta ttcacagaaa gctagatatg ccttaaaaca tactctgccg atctaattac agccttattt ttgtatgcct tttgggcatt ctcctcatgc ttagaaagtt ccaaatgttt ataaaggtaa aatggcagtt tgaagtcaaa tgtcacatag gcaaagcaat caagcaccag gaagtgttta tgaggaaaca acacccaaga tgaattattt ttgagactgt caggaagtaa aataaatagg agcttaagaa agaacatttt gcctgattga gaagcacaac tgaaaccagt agccgctggg gtgttaatgg tagcattctt cttttggcaa tacatttgat ttgttcatga atatattaat cagcattaga gaaatgaatt ataactagac atctgctgtt atcaccatag ttttgtttaa tttgcttcct tttaaataaa cccattggtg aaagtcccaa aaaaaaaaa aaaaaaaa MVCGSPGGMLLLRAGLLALAALCLLRVPGARRAAcEPVRIPLCKSLPWNMTEMPNHLHHSTQDNAILAIEQFEGL

LGTHCSPDLLFFLCAMYAPICTIDFQHEPIKPCKSVCERARQGCEPILIKYRHSWPENLACEELPVYDRGVCISP

EAIVTADGADFPMDSSNGNCRGASSERCKCKPIRATQKTYFRNNYNYVIRAKVKEIKTKCHDVTAVVEVKEILKS

SLVNIPRDTVNLYTSSGCLCPPLNVNEEYIIMGYEDEERSRLLLVEGSIAEKWKDRLGKKVKRWDMKLRHLGLSK

SDSSNSDSTQSQKSGRNSNPRQARNK

TABLE 7

Nucleotide sequence (SEQ ID NO:13) and predicted
amino acid sequence (SEQ ID NO:14) of mfiz
ACCESSION U91904 ggctaacncc atcctgncna tcgancaatt cgaaggtctg ctggncaccc actgcangg ggatctgctc ttcttcctct gcgcnatgta tgcacccatc tgcaccntcg acttccagc ggaacccatc aagccctgca gtctgtgtg cgagcgcgcc cggcagggct gcgagcccat tctcatcaag taccgccact cgtggccgga gagcctagcc tgcgaggagc tgccggtgta cgaccgtggt gtgtgcatct ctccggaggc catcgtcacc gctgacggag cggactttcc tatggattct agtactggac actnccgggg ggcaagcagt gaacgctgca aatgcaagcc tgtcagagcc acacgganga cctngttccg gaacaactac aactatgtga tccgggctaa agttaaagag gtaaaggcaa agtgccatga cgtgactgct gtcgtggagg taaaagagat tctaaaggca tctctggtga acatcccaag ggataccgtc aacctctaca ccacctctgg atgcctctgc ccccacttc atgttaatga ggaatacatc atcatggggtt atgaagacga ggaacgctcc aggctactct tggtcgaggg caccatcgtt gagaagtgga agatcgkmt tggkrwgaar gtcaagcgct gggatatgaa acttcgycat cttggactgg gtaaaacgga tgctagtgac tccactcaga atcagaaggc tgcaggaac tctaatcccc ggccagcagg aagctaagtc ctgaaatgcg aaagaccaca cccattgact ccctactaa gcagtngnat TABLE 7-continued Nucleotide sequence (SEQ ID NO:13) and predicted
amino acid sequence (SEQ ID NO:14) of mfiz
ACCESSION U91904 cgctggatta gcaanggaaa atcgcattat tccantattg tttactacag ataccacgtn gnatgagatg ttanttctgn atcctcnccc cctgnnntct atntggcntc agtctngntc cgcaantctg cccatntcgt ccttctcttc cctnntcnca caggggnanc tnctttcttc tnggaggagn ngnncctccc cnccactatt cntngttntt cccgctcctn ctttgt

ANXILXIXQFEGLLXTHCXGDLLFFLCAMYAPICTXDFQREPIKPCKSVCERARQGCEPILIKYRHSWPESLACE

ELPVYDRGVCISPEAIVTADGADFPMDSSTGHXRGASSERCKCKPVRATRXTXFRNNYNYVIRAKVKEVKAKCHD

VTAVVEVKEILKASLVNIPRDTVNLYTTSGCLCPPLHVNEEYIIMGYEDEERSRLLLVEGTIVEKWKDRXGXKVK

RWDMKLRHLGLGKTDASDSTQNQKAGRNSNPRPAGS barrier, gain entry into an appropriate cell (e.g., a neuron, glial cell, microglial cell, or endothelial cell) and affect the expression of a gene involved in the Wnt signal transduction pathway (e.g., by interacting with the regulatory region or transcription factors involved in gene expression); or such compounds that affect the activity of Wnt protein to the Wnt receptor (e.g., by inhibiting or enhancing the enzymatic activity of the CD) or the activity of some other intracellular factor involved in the Wnt signal transduction pathway, such as, e.g., disheveled or delta-catenin.

Computer modelling and searching technologies permit identification of compounds, or the improvement of already identified compounds, that can modulate Wnt expression or activity. Having identified such a compound or composition, the active sites or regions are identified. Such active sites might typically be ligand binding sites, such as the interaction domains of Wnt with the Wnt receptor. The active site can be identified using methods known in the art including, for example, from the amino acid sequences of peptides, from the nucleotide sequences of nucleic acids, or from study of complexes of the relevant compound or composition with its natural ligand. In the latter case, chemical or X-ray crystallographic methods can be used to find the active site by finding where on the factor the complexed ligand is found.

Next, the three dimensional geometric structure of the active site is determined. This can be done by known methods, including X-ray crystallography, which can determine a complete molecular structure. On the other hand, solid or liquid phase NMR can be used to determine certain intra-molecular distances. Any other experimental method of structure determination can be used to obtain partial or complete geometric structures. The geometric structures can be measured with a complexed ligand, natural or artificial, which may increase the accuracy of the active site structure determined.

If an incomplete or insufficiently accurate structure is determined, the methods of computer based numerical modelling can be used to complete the structure or improve its accuracy. Any recognized modelling method may be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site, either experimentally, by modeling, or by a combination, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. Compounds found from this search are potential Wnt modulating compounds.

Alternatively, these methods can be used to identify improved modulating compounds from an already known modulating compound or ligand. The composition of the known compound can be modified and the structural effects of modification can be determined using the experimental and computer modelling methods described above applied to the new composition. The altered structure is then compared to the active site structure of the compound to determine if an improved fit or interaction results. In this manner, systematic variations in composition, such as by varying side groups, can be quickly evaluated to obtain modified modulating compounds or ligands of improved specificity or activity.

Further experimental and computer modeling methods useful to identify modulating compounds based upon identification of the active sites of Wnt, the Wnt receptor, Wnt, and related transduction and transcription factors will be apparent to those of skill in the art.

Examples of molecular modelling systems are the CHARMm and QUANTA programs (Polygen Corporation, Waltham, Mass.). CHARMm performs the energy minimization and molecular dynamics functions. QUANTA performs the construction, graphic modelling and analysis of molecular structure. QUANTA allows interactive construction, modification, visualization, and analysis of the behavior of molecules with each other.

A number of articles review computer modelling of drugs interactive with specific proteins, such as Rotivinen, et al., 1988, *Acta Pharmaceutical Fennica* 97:159–166; Ripka, New Scientist 54–57 (Jun. 16, 1988); McKinaly and Rossmann, 1989, *Annu. Rev. Pharmacol. Toxiciol.*

29:111–122; Perry and Davies, *OSAR: Quantitative Structure-Activity Relationships in Drug Design* pp. 189–193 (Alan R. Liss, Inc. 1989); Lewis and Dean, 1989, *Proc. R. Soc. Lond.* 236:125–140 and 141–162; and, with respect to a model receptor for nucleic acid components, Askew et al., 1989, *J. Am. Chem. Soc.* 111:1082–1090. Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to design of drugs specific to regions of DNA or RNA, once that region is identified.

Although described above with reference to design and generation of compounds which could alter binding, one could also screen libraries of known compounds, including natural products or synthetic chemicals, and biologically active materials, including proteins, for compounds which are inhibitors or activators.

Compounds identified through the assays described herein may be useful, for example, in lowering extracellular Aβ levels, and in treating Alzheimer's disease.

Methods of Lowering Aβ Peptide Levels

The methods of the invention are useful in treating diseases characterized by high levels of Aβ peptide, e.g., Alzheimer's disease. The invention provides methods of lowering Aβ levels by administering compounds, such as those discussed above, which interact with the Wnt protein and/or the Wnt receptor, or members of the Wnt signal transduction pathway to lower Aβ levels.

The term "fragment", as applied to a peptide, will ordinarily be at least about 10 amino acids, usually about 20 contiguous amino acids, preferably at least 40 contiguous amino acids, more preferably at least 50 contiguous amino acids, and most preferably at least about 60 to 80 or more contiguous amino acids in length. Such peptides can be generated by methods known to those skilled in the art, including proteolytic cleavage of the protein, de novo synthesis of the fragment, or genetic engineering.

Peptide analogs can differ from the native peptides of a Wnt protein by amino acid sequence, or by modifications which do not affect the sequence, or by both. Peptide analogs can have sequences which differ from the wild-type sequence (i.e., the sequence of the homologous portion of the naturally occurring peptide) only by conservative amino acid substitutions, preferably by only one, two, or three, substitutions, for example, substitution of one amino acid for another with similar characteristics (e.g., valine for glycine, arginine for lysine, etc.) or by one or more non-conservative amino acid substitutions, deletions, or insertions which do not abolish the peptide's biological activity.

Modifications (which do not normally alter primary sequence) include in vivo or in vitro chemical derivitization of peptides, e.g., acetylation or carboxylation. Also included are modifications of glycosylation, e.g., those made by modifying the glycosylation patterns of a peptide during its synthesis and processing or in further processing steps, e.g., by exposing the peptide to enzymes which affect glycosylation e.g., mammalian glycosylating or deglycosylating enzymes. Also included are sequences which have phosphorylated amino acid residues, e.g., phosphotyrosine, phosphoserine, or phosphothreonine.

The invention includes analogs in which one or more peptide bonds have been replaced with an alternative type of covalent bond (a "peptide mimetic") which is not susceptible to cleavage by peptidases. Where proteolytic degradation of the peptides following injection into the subject is a problem, replacement of a particularly sensitive peptide bond with a noncleavable peptide mimetic will make the resulting peptide more stable and thus more useful as a therapeutic. Such mimetics, and methods of incorporating them into peptides, are well known in the art. Similarly, the replacement of an L-amino acid residue is a standard way of rendering the peptide less sensitive to proteolysis. Also useful are amino-terminal blocking groups such as t-butyloxycarbonyl, acetyl, theyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4,-dinitrophenyl. Blocking the charged amino- and carboxy-termini of the peptides would have the additional benefit of enhancing passage of the peptide through the hydrophobic cellular membrane and into the cell.

Modification of these peptides to improve penetration of the blood-brain barrier would also be useful. Peptides may be altered to increase lipophilicity (e.g. by esterification to a bulky lipophilic moiety such as cholesteryl) or to supply a cleavable "targetor" moiety that enhances retention on the brain side of the barrier (Bodor et al., *Science* 1992, vol. 257, pp. 1698–1700). Alternatively, the peptide may be linked to an antibody specific for the transferrin receptor, in order to exploit that receptor's role in transporting iron across the blood-brain barrier (Friden et al., *Science*, 1993, vol. 259, pp. 373–377).

Peptides may be administered to the patient intravenously in a pharmaceutically acceptable carrier such as physiological saline. Standard methods for intracellular delivery of peptides can be used, e.g. delivery via liposomes. Such methods are well known to those of ordinary skill in the art. The formulations of this invention are useful for parenteral administration, such as intravenous, subcutaneous, intramuscular, and intraperitoneal.

Therapeutic administration of a peptide intracellularly can also be accomplished using gene therapy, wherein a nucleic acid which includes a promoter operatively linked to a sequence encoding a heterologous peptide is used to generate high-level expression of the peptide in cells transfected with the nucleic acid. DNA or isolated nucleic acid encoding peptides of the invention may be introduced into cells of the patient by standard vectors and/or gene delivery systems. Suitable gene delivery systems may include liposomes, receptor-mediated delivery systems, naked DNA, and viral vectors such as herpes viruses, retroviruses, and adenoviruses, among others.

Pharmaceutically acceptable carriers are biologically compatible vehicles which are suitable for administration to an animal: e.g., physiological saline. A therapeutically effective amount is an amount of the nucleic acid of the invention which is capable of producing a medically desirable result in a treated animal.

As is well known in the medical arts, dosages for any one patient depends upon many factors, including the patient's size, body surface area, age, the particular compound to be administered, sex, time and route of administration, general health, and other drugs being administered concurrently. Dosages for the compounds of the invention will vary, but a preferred dosage for intravenous administration is from approximately $10^6$ to $10^{22}$ copies of the nucleic acid molecule in the case of gene therapy.

The invention will be further described in the following examples, which do not limit the scope of the invention described in the claims.

Example 1
Overexpression of Wnt1 in PC12 and C57MG Cells Leads to an Increase in Aβ Levels A retrovirus encoding the Wnt1 protein was introduced into PC12 cells as described in Mol. Cell. Biol. 14:466, (1995), and twelve independent Wnt1-expressing lines were established. Wnt1 expression in the lines was examined by measuring β-catenin levels. Wnt1 expression in the 12 lines positively correlated with the degree of β catenin stabilization. When Aβ levels in the 12 cell lines were measured by ELISA, it was found that levels of Aβ peptide positively correlated with Wnt1 expression. Aβ levels in the culture media also showed a positive correlation with Wnt1 expression.

An increase in Aβ levels was also observed in the mouse mammary epithelial cell line, C57MG, upon infection with a retrovirus expressing Wnt1 (Mol. Cell. Biol 12:321, (1992). C57MG cells infected with a Wnt5a retrovirus did not show increased Aβ levels.

These results demonstrate that increasing Wnt1 levels in PC12 and C57MG cells causes in increase in Aβ peptide levels.

Example 2
Identification of Aβ-lowering Compounds Using a Cell-Based Screening Assay A PC12 cell line expressing is transfected retrovirus encoding Wnt1 as discussed in Example 1, above. The transfected cells are then cultured in the presence of a test compound. The ability of the compound to inhibit Wnt1 function is determined by measuring β catenin stabilization. Destabilization of β catenin indicates the compound inhibits Wnt1-mediated signal transduction. Aβ levels are then measured in the cells in the presence and absence of the compound. A decrease in Aβ levels in the presence of the compound indicates the compound inhibits expression of the Aβ peptide.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

SEQUENCE LISTING

<160> NUMBER OF SEQ ID NOS: 16

<210> SEQ ID NO 1
<211> LENGTH: 2085
<212> TYPE: DNA
<213> ORGANISM: Homo sapiens
<220> FEATURE:
<221> NAME/KEY: CDS
<222> LOCATION: (1)...(2082)

<400> SEQUENCE: 1

```
atg aga cac aat cga ctg aag gtc ctg atc c tg gga ctc gtc ctc ctg      48
Met Arg His Asn Arg Leu Lys Val Leu Ile L eu Gly Leu Val Leu Leu
 1               5                  10                  15 ctg aca tct tgt cga gcg gat gga ccg ctg c ac agt gcg gat cac ggc      96
Leu Thr Ser Cys Arg Ala Asp Gly Pro Leu H is Ser Ala Asp His Gly
             20                  25                  30 atg ggc gga atg ggc atg ggt ggt cac ggc c tg gac gcg agt ccc gca     144
Met Gly Gly Met Gly Met Gly Gly His Gly L eu Asp Ala Ser Pro Ala
         35                  40                  45 ccc ggt tac gga gtg cca gcc ata ccc aag g at ccc aat ctg cga tgc     192
Pro Gly Tyr Gly Val Pro Ala Ile Pro Lys A sp Pro Asn Leu Arg Cys
     50                  55                  60 gag gag atc acc ata cca atg tgt cgg ggc a tt ggc tac aac atg aca     240
Glu Glu Ile Thr Ile Pro Met Cys Arg Gly I le Gly Tyr Asn Met Thr
 65                  70                  75                  80 tcc ttc ccc aac gaa atg aac cat gag acc c ag gac gaa gcg ggc ctg     288
Ser Phe Pro Asn Glu Met Asn His Glu Thr G ln Asp Glu Ala Gly Leu
                 85                  90                  95 gag gtg cac cag ttc tgg ccc ctg gtg gag a tc aaa tgc tcg ccg gac     336
Glu Val His Gln Phe Trp Pro Leu Val Glu I le Lys Cys Ser Pro Asp
            100                 105                 110 ctc aag ttc ttc ctg tgc agc atg tac acg c cc atc tgc ctg gag gat     384
Leu Lys Phe Phe Leu Cys Ser Met Tyr Thr P ro Ile Cys Leu Glu Asp
        115                 120                 125 tac cac aag ccg ctg ccc gtt tgc cgg agt g tc tgc gag aga gcc cgc     432
Tyr His Lys Pro Leu Pro Val Cys Arg Ser V al Cys Glu Arg Ala Arg
    130                 135                 140
```

-continued

| | | |
|---|---|---|
| tcg gga tgc gca ccc atc atg cag cag tac a gc ttc gaa tgg ccg gag<br>Ser Gly Cys Ala Pro Ile Met Gln Gln Tyr S er Phe Glu Trp Pro Glu<br>145                    150                   155                   160 | 480 |
| aga atg gcg tgc gag cac ttg ccc ctt cat g gt gac ccc gac aat ctg<br>Arg Met Ala Cys Glu His Leu Pro Leu His G ly Asp Pro Asp Asn Leu<br>                165                   170                   175 | 528 |
| tgc atg gaa cag ccc tcg tac acg gag gct g gc agc ggt ggc agc tcg<br>Cys Met Glu Gln Pro Ser Tyr Thr Glu Ala G ly Ser Gly Gly Ser Ser<br>           180                   185                   190 | 576 |
| ggc gga tcg ggt ggc tct ggc agc ggt tcc g gc tcc ggc ggc aaa cgg<br>Gly Gly Ser Gly Gly Ser Gly Ser Gly S ly Ser Gly Gly Lys Arg<br>              195                   200                   205 | 624 |
| aag caa gga ggc agt ggc tcg ggc ggc agt g gg gcc ggc ggc agc agc<br>Lys Gln Gly Gly Ser Gly Ser Gly Gly Ser G ly Ala Gly Gly Ser Ser<br>210                    215                   220 | 672 |
| ggt tcc acc tca acg aag ccg tgc cgc gga c gc aat tca aaa aac tgc<br>Gly Ser Thr Ser Thr Lys Pro Cys Arg Gly A rg Asn Ser Lys Asn Cys<br>225                    230                   235                   240 | 720 |
| caa aat ccc caa gga gaa aag gca agc gga a aa gag tgc agc tgc tcg<br>Gln Asn Pro Gln Gly Glu Lys Ala Ser Gly L ys Glu Cys Ser Cys Ser<br>                245                   250                   255 | 768 |
| tgc cgc tcc cca ctc atc ttc ctg ggg aag g ag cag ctg ctg cag cag<br>Cys Arg Ser Pro Leu Ile Phe Leu Gly Lys G lu Gln Leu Leu Gln Gln<br>           260                   265                   270 | 816 |
| cag tcg cag atg ccc atg atg cac cat cca c ac cac tgg tac atg aac<br>Gln Ser Gln Met Pro Met Met His His Pro H is His Trp Tyr Met Asn<br>              275                   280                   285 | 864 |
| ctc act gtc caa agg atc gcc ggc gtt cca a ac tgc ggc ata ccg tgc<br>Leu Thr Val Gln Arg Ile Ala Gly Val Pro A sn Cys Gly Ile Pro Cys<br>290                    295                   300 | 912 |
| aag ggg ccc ttc ttc agc aac gac gaa aag g at ttc gcc ggc ctc tgg<br>Lys Gly Pro Phe Phe Ser Asn Asp Glu Lys A sp Phe Ala Gly Leu Trp<br>305                    310                   315                   320 | 960 |
| atc gcc ctg tgg tcg gga ctg tgc ttc tgc a gc acg ctc atg acc cta<br>Ile Ala Leu Trp Ser Gly Leu Cys Phe Cys S er Thr Leu Met Thr Leu<br>                325                   330                   335 | 1008 |
| acc aca ttc atc atc gac acc gaa agg ttt a ag tac ccg gag cgg ccc<br>Thr Thr Phe Ile Ile Asp Thr Glu Arg Phe L ys Tyr Pro Glu Arg Pro<br>           340                   345                   350 | 1056 |
| att gtc ttc ctc tcc gcc tgc tac ttc atg g tg gca gtg ggc tac ctg<br>Ile Val Phe Leu Ser Ala Cys Tyr Phe Met V al Ala Val Gly Tyr Leu<br>                355                   360                   365 | 1104 |
| tcg cgc aac ttc ctg cag aac gag gag atc g cc tgc gac ggc ctg ctg<br>Ser Arg Asn Phe Leu Gln Asn Glu Glu Ile A la Cys Asp Gly Leu Leu<br>370                    375                   380 | 1152 |
| ctc cgg gaa agc tcc acg ggt ccg cac tct t gc acc ctg gtc ttc ctg<br>Leu Arg Glu Ser Ser Thr Gly Pro His Ser C ys Thr Leu Val Phe Leu<br>385                    390                   395                   400 | 1200 |
| ctc acc tac ttc ttt ggc atg gcc tcg tcc a tc tgg tgg gtg atc ctc<br>Leu Thr Tyr Phe Phe Gly Met Ala Ser Ser I le Trp Trp Val Ile Leu<br>                405                   410                   415 | 1248 |
| act ttc acc tgg ttc ctg gcc gct ggt ctg a ag tgg ggc aat gag gcc<br>Thr Phe Thr Trp Phe Leu Ala Ala Gly Leu L ys Trp Gly Asn Glu Ala<br>           420                   425                   430 | 1296 |
| atc acc aag cac tcg cag tac ttc cat ctg g cc gcc tgg ttg att ccc<br>Ile Thr Lys His Ser Gln Tyr Phe His Leu A la Ala Trp Leu Ile Pro<br>                435                   440                   445 | 1344 |
| act gtc cag tcc gtg gcc gta ctc ctg ctc t cg gcg gtg gat ggc gat<br>Thr Val Gln Ser Val Ala Val Leu Leu Leu S er Ala Val Asp Gly Asp | 1392 |

```
                450             455             460
ccc att ctg ggc atc tgc tat gtg ggc aac c tc aat ccg gat cac cta    1440
Pro Ile Leu Gly Ile Cys Tyr Val Gly Asn L eu Asn Pro Asp His Leu
465                 470                 475                 480 aag acc ttt gtg ctg gcc ccg ctc ttc gtt t ac ctc gta atc ggc acc    1488
Lys Thr Phe Val Leu Ala Pro Leu Phe Val T yr Leu Val Ile Gly Thr
                        485                 490                 495 acc ttc ctg atg gcc ggc ttt gtg tcc ctc t tc cgc atc cgc tcg gtt    1536
Thr Phe Leu Met Ala Gly Phe Val Ser Leu P he Arg Ile Arg Ser Val
                500                 505                 510 atc aag caa cag ggc ggt gta gga gct ggt g tc aag gcg gac aag ctg    1584
Ile Lys Gln Gln Gly Gly Val Gly Ala Gly V al Lys Ala Asp Lys Leu
            515                 520                 525 gag aaa ctg atg atc agg att ggc atc ttc t cg gtg ctc tac acg gtg    1632
Glu Lys Leu Met Ile Arg Ile Gly Ile Phe S er Val Leu Tyr Thr Val
        530                 535                 540 ccg gcc acc ata gtt atc gga tgt tac ctg t ac gaa gca gcc tac ttt    1680
Pro Ala Thr Ile Val Ile Gly Cys Tyr Leu T yr Glu Ala Ala Tyr Phe
545                 550                 555                 560 gag gac tgg atc aag gcc ctg gcc tgt cca t gc gcc cag gtg aag ggt    1728
Glu Asp Trp Ile Lys Ala Leu Ala Cys Pro C ys Ala Gln Val Lys Gly
                565                 570                 575 ccc ggc aag aag cct ctc tac tcg gtc ctg a tg ctc aag tac ttc atg    1776
Pro Gly Lys Lys Pro Leu Tyr Ser Val Leu M et Leu Lys Tyr Phe Met
                580                 585                 590 gcc ctg gcc gtg ggc atc acc tcg ggc gtg t gg atc tgg tct ggc aag    1824
Ala Leu Ala Val Gly Ile Thr Ser Gly Val T rp Ile Trp Ser Gly Lys
            595                 600                 605 acg ctg gag agc tgg cga cgc ttc tgg cgg a ga ctc cta gga gcg ccg    1872
Thr Leu Glu Ser Trp Arg Arg Phe Trp Arg A rg Leu Leu Gly Ala Pro
        610                 615                 620 gac cgc acg ggc gcc aac cag gcg ctg atc a ag cag cgg cct ccg atc    1920
Asp Arg Thr Gly Ala Asn Gln Ala Leu Ile L ys Gln Arg Pro Pro Ile
625                 630                 635                 640 ccg cat ccc tat gcc gga tct gga atg ggc a tg ccc gtg ggc tcg gcg    1968
Pro His Pro Tyr Ala Gly Ser Gly Met Gly M et Pro Val Gly Ser Ala
                645                 650                 655 gcg ggc tcc ctg ctg gcc acg ccc tac acc c ag gcg ggc gga gcc tcg    2016
Ala Gly Ser Leu Leu Ala Thr Pro Tyr Thr G ln Ala Gly Gly Ala Ser
                660                 665                 670 gtg gcc tcc acc agc cac cac cac ctg cac c ac cac gtt ctc aag cag    2064
Val Ala Ser Thr Ser His His His Leu His H is His Val Leu Lys Gln
            675                 680                 685 ccg gcg gcc agc cac gta tga                                          2085
Pro Ala Ala Ser His Val
        690

<210> SEQ ID NO 2
<211> LENGTH: 694
<212> TYPE: PRT
<213> ORGANISM: Homo sapiens

<400> SEQUENCE: 2

Met Arg His Asn Arg Leu Lys Val Leu Ile L eu Gly Leu Val Leu Leu
1               5                   10                  15

Leu Thr Ser Cys Arg Ala Asp Gly Pro Leu H is Ser Ala Asp His Gly
                20                  25                  30

Met Gly Gly Met Gly Met Gly Gly His Gly L eu Asp Ala Ser Pro Ala
        35                  40                  45
```

-continued

```
Pro Gly Tyr Gly Val Pro Ala Ile Pro Lys Asp Pro Asn Leu Arg Cys
    50                  55                  60
Glu Glu Ile Thr Ile Pro Met Cys Arg Gly Ile Gly Tyr Asn Met Thr
 65                  70                  75                  80
Ser Phe Pro Asn Glu Met Asn His Glu Thr Gln Asp Glu Ala Gly Leu
                 85                  90                  95
Glu Val His Gln Phe Trp Pro Leu Val Glu Ile Lys Cys Ser Pro Asp
            100                 105                 110
Leu Lys Phe Phe Leu Cys Ser Met Tyr Thr Pro Ile Cys Leu Glu Asp
        115                 120                 125
Tyr His Lys Pro Leu Pro Val Cys Arg Ser Val Cys Glu Arg Ala Arg
    130                 135                 140
Ser Gly Cys Ala Pro Ile Met Gln Gln Tyr Ser Phe Glu Trp Pro Glu
145                 150                 155                 160
Arg Met Ala Cys Glu His Leu Pro Leu His Gly Asp Pro Asp Asn Leu
                165                 170                 175
Cys Met Glu Gln Pro Ser Tyr Thr Glu Ala Gly Ser Gly Gly Ser Ser
            180                 185                 190
Gly Gly Ser Gly Gly Ser Gly Ser Gly Ser Gly Gly Lys Arg
        195                 200                 205
Lys Gln Gly Gly Ser Gly Ser Gly Ser Gly Ala Gly Ser Ser
    210                 215                 220
Gly Ser Thr Ser Thr Lys Pro Cys Arg Gly Arg Asn Ser Lys Asn Cys
225                 230                 235                 240
Gln Asn Pro Gln Gly Glu Lys Ala Ser Gly Lys Glu Cys Ser Cys Ser
                245                 250                 255
Cys Arg Ser Pro Leu Ile Phe Leu Gly Lys Glu Gln Leu Leu Gln Gln
            260                 265                 270
Gln Ser Gln Met Pro Met Met His His Pro His His Trp Tyr Met Asn
        275                 280                 285
Leu Thr Val Gln Arg Ile Ala Gly Val Pro Asn Cys Gly Ile Pro Cys
    290                 295                 300
Lys Gly Pro Phe Phe Ser Asn Asp Glu Lys Asp Phe Ala Gly Leu Trp
305                 310                 315                 320
Ile Ala Leu Trp Ser Gly Leu Cys Phe Cys Ser Thr Leu Met Thr Leu
                325                 330                 335
Thr Thr Phe Ile Ile Asp Thr Glu Arg Phe Lys Tyr Pro Glu Arg Pro
            340                 345                 350
Ile Val Phe Leu Ser Ala Cys Tyr Phe Met Val Ala Val Gly Tyr Leu
        355                 360                 365
Ser Arg Asn Phe Leu Gln Asn Glu Glu Ile Ala Cys Asp Gly Leu Leu
    370                 375                 380
Leu Arg Glu Ser Ser Thr Gly Pro His Ser Cys Thr Leu Val Phe Leu
385                 390                 395                 400
Leu Thr Tyr Phe Phe Gly Met Ala Ser Ser Ile Trp Trp Val Ile Leu
                405                 410                 415
Thr Phe Thr Trp Phe Leu Ala Ala Gly Leu Lys Trp Gly Asn Glu Ala
            420                 425                 430
Ile Thr Lys His Ser Gln Tyr Phe His Leu Ala Ala Trp Leu Ile Pro
        435                 440                 445
Thr Val Gln Ser Val Ala Val Leu Leu Leu Ser Ala Val Asp Gly Asp
    450                 455                 460
Pro Ile Leu Gly Ile Cys Tyr Val Gly Asn Leu Asn Pro Asp His Leu
```

```
                465                 470                 475                 480
Lys Thr Phe Val Leu Ala Pro Leu Phe Val Tyr Leu Val Ile Gly Thr
                    485                 490                 495
Thr Phe Leu Met Ala Gly Phe Val Ser Leu Phe Arg Ile Arg Ser Val
                500                 505                 510
Ile Lys Gln Gln Gly Gly Val Gly Ala Gly Val Lys Ala Asp Lys Leu
            515                 520                 525
Glu Lys Leu Met Ile Arg Ile Gly Ile Phe Ser Val Leu Tyr Thr Val
        530                 535                 540
Pro Ala Thr Ile Val Ile Gly Cys Tyr Leu Tyr Glu Ala Ala Tyr Phe
545                 550                 555                 560
Glu Asp Trp Ile Lys Ala Leu Ala Cys Pro Cys Ala Gln Val Lys Gly
                565                 570                 575
Pro Gly Lys Lys Pro Leu Tyr Ser Val Leu Met Leu Lys Tyr Phe Met
            580                 585                 590
Ala Leu Ala Val Gly Ile Thr Ser Gly Val Trp Ile Trp Ser Gly Lys
        595                 600                 605
Thr Leu Glu Ser Trp Arg Arg Phe Trp Arg Arg Leu Leu Gly Ala Pro
    610                 615                 620
Asp Arg Thr Gly Ala Asn Gln Ala Leu Ile Lys Gln Arg Pro Pro Ile
625                 630                 635                 640
Pro His Pro Tyr Ala Gly Ser Gly Met Gly Met Pro Val Gly Ser Ala
                645                 650                 655
Ala Gly Ser Leu Leu Ala Thr Pro Tyr Thr Gln Ala Gly Gly Ala Ser
            660                 665                 670
Val Ala Ser Thr Ser His His His Leu His His His Val Leu Lys Gln
        675                 680                 685
Pro Ala Ala Ser His Val
    690

<210> SEQ ID NO 3
<211> LENGTH: 2334
<212> TYPE: DNA
<213> ORGANISM: Homo sapiens
<220> FEATURE:
<221> NAME/KEY: CDS
<222> LOCATION: (321)...(2075)

<400> SEQUENCE: 3
acccagggac ggaggaccca ggctggcttg gggactgtct gctcttctcg g cgggagccg        60 tggagagtcc tttccctgga atccgagccc taaccgtctc tccccagccc t atccggcga       120 ggagcggagc gctgccagcg gaggcagcgc cttcccgaag cagtttatct t tggacggtt       180 ttctttaaag gaaaaacgaa ccaacaggtt gccagccccg cgccacaca c gagacgccg       240 gagggagaag ccccggcccg gattcctctg cctgtgtgcg tccctcgcgg g ctgctggag       300 gcgaggggag ggaggggggcg atg gct cgg cct gac cca t cc gcg ccg ccc tcg     353
                         Met Ala Arg Pro Asp Pro Ser Ala Pro Pro Ser
                          1               5                  10 ctg ttg ctg ctg ctc ctg gcg cag ctg gtg g gc cgg gcg gcc gcc gcg        401
Leu Leu Leu Leu Leu Leu Ala Gln Leu Val Gly Arg Ala Ala Ala Ala
            15                  20                  25 tcc aag gcc ccg gtg tgc cag gaa atc acg g tg ccc atg tgc cgc ggc        449
Ser Lys Ala Pro Val Cys Gln Glu Ile Thr Val Pro Met Cys Arg Gly
        30                  35                  40 atc ggc tac aac ctg acg cac atg ccc aac c ag ttc aac cac gac acg       497
Ile Gly Tyr Asn Leu Thr His Met Pro Asn Gln Phe Asn His Asp Thr
```

```
                        -continued
        45                  50                  55
cag gac gag gcg ggc ctg gag gtg cac cag t tc tgg ccg ctg gtg gag      545
Gln Asp Glu Ala Gly Leu Glu Val His Gln P he Trp Pro Leu Val Glu
 60                  65                  70                  75 atc caa tgc tcg ccg gac ctg cgc ttc ttc c ta tgc act atg tac acg      593
Ile Gln Cys Ser Pro Asp Leu Arg Phe Phe L eu Cys Thr Met Tyr Thr
                 80                  85                  90 ccc atc tgt ctg ccc gac tac cac aag ccg c tg ccg ccc tgc cgc tcg      641
Pro Ile Cys Leu Pro Asp Tyr His Lys Pro L eu Pro Pro Cys Arg Ser
                 95                  100                 105 gtg tgc gag cgc gcc aag gcc ggc tgc tcg c cg ctg atg cgc cag tac      689
Val Cys Glu Arg Ala Lys Ala Gly Cys Ser P ro Leu Met Arg Gln Tyr
             110                 115                 120 ggc ttc gcc tgg ccc gag cgc atg agc tgc g ac cgc ctc ccg gtg ctg      737
Gly Phe Ala Trp Pro Glu Arg Met Ser Cys A sp Arg Leu Pro Val Leu
         125                 130                 135 ggc cgc gac gcc gag gtc ctc tgc atg gat t ac aac cgc agc gag gcc      785
Gly Arg Asp Ala Glu Val Leu Cys Met Asp T yr Asn Arg Ser Glu Ala
140                 145                 150                 155 acc acg gcg ccc ccc agg cct ttc cca gcc a ag ccc acc ctt cca ggc      833
Thr Thr Ala Pro Pro Arg Pro Phe Pro Ala L ys Pro Thr Leu Pro Gly
                 160                 165                 170 ccg cca ggg gcg ccg gcc tcg ggg ggc gaa t gc ccc gct ggg ggc ccg      881
Pro Pro Gly Ala Pro Ala Ser Gly Gly Glu C ys Pro Ala Gly Gly Pro
             175                 180                 185 ttc gtg tgc aag tgt cgc gag ccc ttc gtg c cc att ctg aag gag tca      929
Phe Val Cys Lys Cys Arg Glu Pro Phe Val P ro Ile Leu Lys Glu Ser
         190                 195                 200 cac ccg ctc tac aac aag gtg cgg acg ggc c ag gtg ccc aac tgc gcg      977
His Pro Leu Tyr Asn Lys Val Arg Thr Gly G ln Val Pro Asn Cys Ala
205                 210                 215 gta ccc tgc tac cag ccg tcc ttc agt gcc g ac gag cgc acg ttc gcc     1025
Val Pro Cys Tyr Gln Pro Ser Phe Ser Ala A sp Glu Arg Thr Phe Ala
220                 225                 230                 235 acc ttc tgg ata ggc ctg tgg tcg gtg ctg t gc ttc atc tcc acg tcc     1073
Thr Phe Trp Ile Gly Leu Trp Ser Val Leu C ys Phe Ile Ser Thr Ser
                 240                 245                 250 acc aca gtg gcc acc ttc ctc atc gac atg g ac acg ttc cgc tat cct     1121
Thr Thr Val Ala Thr Phe Leu Ile Asp Met A sp Thr Phe Arg Tyr Pro
             255                 260                 265 gag cgc ccc atc atc ttc ctg tca gcc tgc t ac ctg tgc gtg tcg ctg     1169
Glu Arg Pro Ile Ile Phe Leu Ser Ala Cys T yr Leu Cys Val Ser Leu
         270                 275                 280 ggc ttc ctg gtg cgt ctg gtc gtg ggc cat g cc agc gtg gcc tgc agc     1217
Gly Phe Leu Val Arg Leu Val Val Gly His A la Ser Val Ala Cys Ser
     285                 290                 295 cgc gag cac aac cac atc cac tac gag acc a cg ggc cct gca ctg tgc     1265
Arg Glu His Asn His Ile His Tyr Glu Thr T hr Gly Pro Ala Leu Cys
300                 305                 310                 315 acc atc gtc ttc ctc ctg gtc tac ttc ttc g gc atg gcc agc tcc atc     1313
Thr Ile Val Phe Leu Leu Val Tyr Phe Phe G ly Met Ala Ser Ser Ile
                 320                 325                 330 tgg tgg gtc atc ctg tcg ctc acc tgg ttc c tg gcc gcc gcg atg aag     1361
Trp Trp Val Ile Leu Ser Leu Thr Trp Phe L eu Ala Ala Ala Met Lys
             335                 340                 345 tgg ggc aac gag gcc atc gcg ggc tac ggc c ag tac ttc cac ctg gct     1409
Trp Gly Asn Glu Ala Ile Ala Gly Tyr Gly G ln Tyr Phe His Leu Ala
         350                 355                 360 gcg tgg ctc atc ccc agc gtc aag tcc atc a cg gca ctg gcg ctg agc     1457
```

```
Ala Trp Leu Ile Pro Ser Val Lys Ser Ile Thr Ala Leu Ala Leu Ser
    365                 370                 375 tcc gtg gac ggg gac cca gtg gcc ggc atc tgc tac gtg ggc aac cag       1505
Ser Val Asp Gly Asp Pro Val Ala Gly Ile Cys Tyr Val Gly Asn Gln
380                 385                 390                 395 aac ctg aac tcg ctg cgg cgc ttc gtg ctg ggc ccg ctg gtg ctc tac       1553
Asn Leu Asn Ser Leu Arg Arg Phe Val Leu Gly Pro Leu Val Leu Tyr
                400                 405                 410 ctg ctg gtg ggc acg ctc ttc ctg ctg gcg ggc ttc gtg tcg ctc ttc       1601
Leu Leu Val Gly Thr Leu Phe Leu Leu Ala Gly Phe Val Ser Leu Phe
            415                 420                 425 cgc atc cgc agc gtc atc aag cag ggc ggc acc aag acg gac aag ctg       1649
Arg Ile Arg Ser Val Ile Lys Gln Gly Gly Thr Lys Thr Asp Lys Leu
        430                 435                 440 gag aag ctc atg atc cgc atc ggc atc ttc acg ctg ctc tac acg gtc       1697
Glu Lys Leu Met Ile Arg Ile Gly Ile Phe Thr Leu Leu Tyr Thr Val
    445                 450                 455 ccc gcc agc att gtg gtg gcc tgc tac ctg tac gag cag cac tac cgc       1745
Pro Ala Ser Ile Val Val Ala Cys Tyr Leu Tyr Glu Gln His Tyr Arg
460                 465                 470                 475 gag agc tgg gag gcg gcg ctc acc tgc gcc tgc ccg ggc cac gac acc       1793
Glu Ser Trp Glu Ala Ala Leu Thr Cys Ala Cys Pro Gly His Asp Thr
                480                 485                 490 ggc cag ccg cgc gcc aag ccc gag tac tgg gtg ctc atg ctc aag tac       1841
Gly Gln Pro Arg Ala Lys Pro Glu Tyr Trp Val Leu Met Leu Lys Tyr
            495                 500                 505 ttc atg tgc ctg gtg gtg ggc atc acg tcg ggc gtc tgg atc tgg tcg       1889
Phe Met Cys Leu Val Val Gly Ile Thr Ser Gly Val Trp Ile Trp Ser
        510                 515                 520 ggc aag acg gtg gag tcg tgg cgg cgt ttc acc agc cgc tgc tgc tgc       1937
Gly Lys Thr Val Glu Ser Trp Arg Arg Phe Thr Ser Arg Cys Cys Cys
    525                 530                 535 cgc ccg cgg cgc ggc cac aag agc ggg ggc gcc atg gcc gca ggg gac       1985
Arg Pro Arg Arg Gly His Lys Ser Gly Gly Ala Met Ala Ala Gly Asp
540                 545                 550                 555 tac ccc gag gcg agc gcc gcg ctc aca ggc agg acc ggg ccg ccg ggc       2033
Tyr Pro Glu Ala Ser Ala Ala Leu Thr Gly Arg Thr Gly Pro Pro Gly
                560                 565                 570 ccc gcc gcc acc tac cac aag cag gtg tcc ctg tcg cac gtg                2075
Pro Ala Ala Thr Tyr His Lys Gln Val Ser Leu Ser His Val
            575                 580                 585 taggaggctg ccgccgaggg actcggccgg agagctgagg ggaggggggc gttttgtttg      2135
gtagttttgc caaggtcact tccgtttacc ttcatggtgc tgttgccccc tcccgcggcg      2195
acttggagag agggaagagg ggcgttttcg aggaagaacc tgtcccaggt cttctccaag      2255
gggcccagct cacgtgtatt ctattttgcg tttcttacct gccttcttta tgggaaccct      2315 cttttaatt tatatgtat                                                   2334
```

<210> SEQ ID NO 4
<211> LENGTH: 585
<212> TYPE: PRT
<213> ORGANISM: Homo sapiens

<400> SEQUENCE: 4

```
Met Ala Arg Pro Asp Pro Ser Ala Pro Pro Ser Leu Leu Leu Leu Leu
1               5                   10                  15

Leu Ala Gln Leu Val Gly Arg Ala Ala Ala Ser Lys Ala Pro Val
            20                  25                  30
```

-continued

```
Cys Gln Glu Ile Thr Val Pro Met Cys Arg Gly Ile Gly Tyr Asn Leu
        35                  40                  45
Thr His Met Pro Asn Gln Phe Asn His Asp Thr Gln Asp Glu Ala Gly
    50                  55                  60
Leu Glu Val His Gln Phe Trp Pro Leu Val Glu Ile Gln Cys Ser Pro
65                  70                  75                  80
Asp Leu Arg Phe Phe Leu Cys Thr Met Tyr Thr Pro Ile Cys Leu Pro
                85                  90                  95
Asp Tyr His Lys Pro Leu Pro Pro Cys Arg Ser Val Cys Glu Arg Ala
            100                 105                 110
Lys Ala Gly Cys Ser Pro Leu Met Arg Gln Tyr Gly Phe Ala Trp Pro
            115                 120                 125
Glu Arg Met Ser Cys Asp Arg Leu Pro Val Leu Gly Arg Asp Ala Glu
        130                 135                 140
Val Leu Cys Met Asp Tyr Asn Arg Ser Glu Ala Thr Thr Ala Pro Pro
145                 150                 155                 160
Arg Pro Phe Pro Ala Lys Pro Thr Leu Pro Gly Pro Pro Gly Ala Pro
                165                 170                 175
Ala Ser Gly Gly Glu Cys Pro Ala Gly Gly Pro Phe Val Cys Lys Cys
            180                 185                 190
Arg Glu Pro Phe Val Pro Ile Leu Lys Glu Ser His Pro Leu Tyr Asn
            195                 200                 205
Lys Val Arg Thr Gly Gln Val Pro Asn Cys Ala Val Pro Cys Tyr Gln
        210                 215                 220
Pro Ser Phe Ser Ala Asp Glu Arg Thr Phe Ala Thr Phe Trp Ile Gly
225                 230                 235                 240
Leu Trp Ser Val Leu Cys Phe Ile Ser Thr Ser Thr Thr Val Ala Thr
                245                 250                 255
Phe Leu Ile Asp Met Asp Thr Phe Arg Tyr Pro Glu Arg Pro Ile Ile
            260                 265                 270
Phe Leu Ser Ala Cys Tyr Leu Cys Val Ser Leu Gly Phe Leu Val Arg
            275                 280                 285
Leu Val Val Gly His Ala Ser Val Ala Cys Ser Arg Glu His Asn His
        290                 295                 300
Ile His Tyr Glu Thr Thr Gly Pro Ala Leu Cys Thr Ile Val Phe Leu
305                 310                 315                 320
Leu Val Tyr Phe Phe Gly Met Ala Ser Ser Ile Trp Trp Val Ile Leu
                325                 330                 335
Ser Leu Thr Trp Phe Leu Ala Ala Ala Met Lys Trp Gly Asn Glu Ala
            340                 345                 350
Ile Ala Gly Tyr Gly Gln Tyr Phe His Leu Ala Ala Trp Leu Ile Pro
            355                 360                 365
Ser Val Lys Ser Ile Thr Ala Leu Ala Leu Ser Ser Val Asp Gly Asp
        370                 375                 380
Pro Val Ala Gly Ile Cys Tyr Val Gly Asn Gln Asn Leu Asn Ser Leu
385                 390                 395                 400
Arg Arg Phe Val Leu Gly Pro Leu Val Leu Tyr Leu Leu Val Gly Thr
                405                 410                 415
Leu Phe Leu Leu Ala Gly Phe Val Ser Leu Phe Arg Ile Arg Ser Val
            420                 425                 430
Ile Lys Gln Gly Gly Thr Lys Thr Asp Lys Leu Glu Lys Leu Met Ile
        435                 440                 445
Arg Ile Gly Ile Phe Thr Leu Leu Tyr Thr Val Pro Ala Ser Ile Val
```

```
                450             455             460
Val Ala Cys Tyr Leu Tyr Glu Gln His Tyr A rg Glu Ser Trp Glu Ala
465                 470                 475                 480

Ala Leu Thr Cys Ala Cys Pro Gly His Asp T hr Gly Gln Pro Arg Ala
                485                 490                 495

Lys Pro Glu Tyr Trp Val Leu Met Leu Lys T yr Phe Met Cys Leu Val
                500                 505                 510

Val Gly Ile Thr Ser Gly Val Trp Ile Trp S er Gly Lys Thr Val Glu
            515                 520                 525

Ser Trp Arg Arg Phe Thr Ser Arg Cys Cys C ys Arg Pro Arg Arg Gly
            530                 535                 540

His Lys Ser Gly Gly Ala Met Ala Ala Gly A sp Tyr Pro Glu Ala Ser
545                 550                 555                 560

Ala Ala Leu Thr Gly Arg Thr Gly Pro Pro G ly Pro Ala Ala Thr Tyr
                565                 570                 575

His Lys Gln Val Ser Leu Ser His Val
                580                 585

<210> SEQ ID NO 5
<211> LENGTH: 2831
<212> TYPE: DNA
<213> ORGANISM: Homo sapiens
<220> FEATURE:
<221> NAME/KEY: CDS
<222> LOCATION: (328)...(1938)
<221> NAME/KEY: misc_feature
<222> LOCATION: (1)...(2831)
<223> OTHER INFORMATION: n = A,T,C or G

<400> SEQUENCE: 5
tcgacctcaa cacaaagacc tgggtcgtga gacacacgcg tagagtcagg c ggcttcccc         60 gaaaaccgga ctcggccggc gccgagtctg ggtccccgcc ttcaaccatg a ccctagcaa        120 tccatccctc ggcccgggct ccggacgtct gatattccgc acattctcgt a caactgctg       180 gagaggcgac tgctgcccccc ttgtcgccct tggcgcctta ccgcattccc t atccggagt      240 tgggagcagc gcggccaccg gcgcccctgt gcaaactggg ggtgtctgct a gatcagcct       300 ctgccgctgc tgcccgcagc tctggcc atg gcc tgg ccg ggc aca ggg ccg agc        354
                                Met Ala Trp Pr o Gly Thr Gly Pro Ser
                                 1               5 agc cgg ggg gcg cct gga ggc gtc ggg ctc a gg ctg ggg ctg ctg ctg         402
Ser Arg Gly Ala Pro Gly Gly Val Gly Leu A rg Leu Gly Leu Leu Leu
 10              15                  20                  25 cag ttc ctc ctg ctc ctg cgg ccg aca ctg g gg ttc ggg gac gag gag         450
Gln Phe Leu Leu Leu Leu Arg Pro Thr Leu G ly Phe Gly Asp Glu Glu
             30                  35                  40 gag cgg cgc tgc gac ccc atc cgc atc gcc a tg tgc cag aac ctc ggc         498
Glu Arg Arg Cys Asp Pro Ile Arg Ile Ala M et Cys Gln Asn Leu Gly
             45                  50                  55 tac aac gtg acc aag atg ccc aac tta gtg g ga cac gag ctg cag aca         546
Tyr Asn Val Thr Lys Met Pro Asn Leu Val G ly His Glu Leu Gln Thr
         60                  65                  70 gac gcc gag ctg cag ctg aca act ttc acg c cg ctc atc cag tac ggc         594
Asp Ala Glu Leu Gln Leu Thr Thr Phe Thr P ro Leu Ile Gln Tyr Gly
     75                  80                  85 tgc tcc agc cag ctg cag ttc ttc ctt tgt t cg gtt tat gtg cca atg         642
Cys Ser Ser Gln Leu Gln Phe Phe Leu Cys S er Val Tyr Val Pro Met
 90                  95                 100                 105 tgc aca gag aag atc aac atc ccc atc ggc c cg tgc ggt ggc atg tgc         690
```

```
                Cys Thr Glu Lys Ile Asn Ile Pro Ile Gly Pro Cys Gly Gly Met Cys
                                110                 115                 120 ctt tca gtc aag aga cgc tgt gaa cca gtc ctg aga gaa ttt ggg ttt        738
Leu Ser Val Lys Arg Arg Cys Glu Pro Val Leu Arg Glu Phe Gly Phe
            125                 130                 135 gcc tgg ccc gac acc ctg aac tgc agc aag ttc ccg ccc cag aac gac        786
Ala Trp Pro Asp Thr Leu Asn Cys Ser Lys Phe Pro Pro Gln Asn Asp
            140                 145                 150 cac aac cac atg tgc atg gaa gga cca ggt gat gaa gag gtt ccc ttg        834
His Asn His Met Cys Met Glu Gly Pro Gly Asp Glu Glu Val Pro Leu
            155                 160                 165 ccc cac aag act ccc atc cag ccc ggg gaa gag tgc cac tcc gtg gga        882
Pro His Lys Thr Pro Ile Gln Pro Gly Glu Glu Cys His Ser Val Gly
170             175                 180                 185 agc aat tct gat cag tac atc tgg gtg aag agg agc ctg aac tgt gtt        930
Ser Asn Ser Asp Gln Tyr Ile Trp Val Lys Arg Ser Leu Asn Cys Val
                190                 195                 200 ctc aag tgt ggc tac gat gct ggc ttg tac agc cgc tca gct aag gag        978
Leu Lys Cys Gly Tyr Asp Ala Gly Leu Tyr Ser Arg Ser Ala Lys Glu
                205                 210                 215 ttc acg gat att tgg atg gct gtg tgg gcc agc ctc tgc ttc atc tcc       1026
Phe Thr Asp Ile Trp Met Ala Val Trp Ala Ser Leu Cys Phe Ile Ser
            220                 225                 230 acc acc ttc acc gtg ctg acc ttc ctg att gat tca tcc agg ttt tct       1074
Thr Thr Phe Thr Val Leu Thr Phe Leu Ile Asp Ser Ser Arg Phe Ser
            235                 240                 245 tac cct gag cgc ccc atc ata ttt ctc agt atg tgc tat aat att tat       1122
Tyr Pro Glu Arg Pro Ile Ile Phe Leu Ser Met Cys Tyr Asn Ile Tyr
250             255                 260                 265 agc att gct tat att gtt cgg ctg act gta ggc cgg gaa agg ata tcc       1170
Ser Ile Ala Tyr Ile Val Arg Leu Thr Val Gly Arg Glu Arg Ile Ser
                270                 275                 280 tgt gat ttt gaa gag gcg gca gag ccc gtt ctc atc caa gaa gga ctt       1218
Cys Asp Phe Glu Glu Ala Ala Glu Pro Val Leu Ile Gln Glu Gly Leu
                285                 290                 295 aag aac aca gga tgt gca ata att ttc ttg ctg atg tac ttt ttt gga       1266
Lys Asn Thr Gly Cys Ala Ile Ile Phe Leu Leu Met Tyr Phe Phe Gly
            300                 305                 310 atg gcc agc tcc att tgg tgg gtt att ctg aca ctc act tgg ttt ttg       1314
Met Ala Ser Ser Ile Trp Trp Val Ile Leu Thr Leu Thr Trp Phe Leu
315             320                 325 gca gcc gga ctc aag tgg ggt cat gaa gcc att gaa atg cac agt tct       1362
Ala Ala Gly Leu Lys Trp Gly His Glu Ala Ile Glu Met His Ser Ser
330             335                 340                 345 tat ttc cac atc gca gcc tgg gct att ccc gca gtg aaa acc att gtc       1410
Tyr Phe His Ile Ala Ala Trp Ala Ile Pro Ala Val Lys Thr Ile Val
            350                 355                 360 atc ttg att atg aga cta gtg gat gcc gat gaa ctg act ggc ttg tgc       1458
Ile Leu Ile Met Arg Leu Val Asp Ala Asp Glu Leu Thr Gly Leu Cys
            365                 370                 375 tat gtt ggg aac caa aac cta gat gcc ctc act ggc ttt gtg gtg gct       1506
Tyr Val Gly Asn Gln Asn Leu Asp Ala Leu Thr Gly Phe Val Val Ala
            380                 385                 390 cct ctc ttt acg tat ttg gtg att gga acg ctg ttc att gcg gcg ggt       1554
Pro Leu Phe Thr Tyr Leu Val Ile Gly Thr Leu Phe Ile Ala Ala Gly
            395                 400                 405 ttg gtg gcc tta ttc aaa att cgg tcc aat ctt caa aaa gac ggg aca       1602
Leu Val Ala Leu Phe Lys Ile Arg Ser Asn Leu Gln Lys Asp Gly Thr
410             415                 420                 425
```

-continued

```
aag aca gac aag ttg gaa agg cta atg gtc a ag atc ggg gtc ttc tca        1650
Lys Thr Asp Lys Leu Glu Arg Leu Met Val L ys Ile Gly Val Phe Ser
                430                435                440 gta ctg tac acg gtt cct gca acc tgt gtg a tt gcc tgt tat ttc tat        1698
Val Leu Tyr Thr Val Pro Ala Thr Cys Val I le Ala Cys Tyr Phe Tyr
                445                450                455 gaa atc tca aac tgg gca ctc ttt cga tat t ct gca gat gac tca aac        1746
Glu Ile Ser Asn Trp Ala Leu Phe Arg Tyr S er Ala Asp Asp Ser Asn
                460                465                470 atg gca gtt gaa atg ttg aaa att ttt atg t ct ttg ctc gtg ggc atc        1794
Met Ala Val Glu Met Leu Lys Ile Phe Met S er Leu Leu Val Gly Ile
        475                480                485 act tca ggc atg tgg att tgg tct gcc aaa a ct ctt cac acg tgg caa        1842
Thr Ser Gly Met Trp Ile Trp Ser Ala Lys T hr Leu His Thr Trp Gln
490                495                500                505 aag tgt tct aac cga ttg gtg aat tct ggg a ag gta aag aga gag aag        1890
Lys Cys Ser Asn Arg Leu Val Asn Ser Gly L ys Val Lys Arg Glu Lys
                510                515                520 agg ggg aat ggt tgg gtg aag cca gga aaa g gc aac gag act gtg gta        1938
Arg Gly Asn Gly Trp Val Lys Pro Gly Lys G ly Asn Glu Thr Val Val
                525                530                535 taagactagc cggcttcctc gttcctcatt gtgaaggaag tgatgcaggg a atctcagtt      1998 tgaacaaact tagaaacact tcagcccaca cacacccacg tcagcccacc a ccactcacc     2058 caactcagca tcagaagacc aatggcttca ctgcagactt tggaatggtc c aaaatggaa     2118 aagccagtta agaggttttc aaagctgtga aaaatcaaaa tgttgatcac t ttagcaggt     2178 cacagcttgg agtccgtgga ggtcccgcct agattcctga agcccagggt g atagtgttt     2238 gctcctactg ggtgggattt caactgtgag ttgataacat gcaaggagaa a gattaattt    2298 ttaaaaccct tttaaatttt aaatagtaac taaggtcttg cagatagcaa a gtgatctat    2358 aaacactgga aatgctgggt tgggagacgt gttgcagagt ttttatatng t ttnnctggt    2418 ctaacataaa catcttctgg cctacactgt ctgctgttta gaactctgta g cgcactccc    2478 agaggtggtg tcaaaatcct tcagtgcctt gtcgtaaaac agaattgttt g agcaaacaa    2538 aagtactgta ctaacacacg taaggtatcc agtggatttc tctctcctga a atttcaaca   2598 tccctaattc taggcagccc ctgttttctt cactttaaac taatgactca a aaaaaaaa    2658 ggttattttt ataggatttt tttttgcact gcagcatgcc taatgagagg a aaaggaggt   2718 gatcacttct gacaatcact taattcagag aaaaatgaga tttgctaatt g acttacctt   2778 ccgaccccta gagaccctat tgcattaagc aatgtttaag caattgggga c tt           2831
```

<210> SEQ ID NO 6
<211> LENGTH: 537
<212> TYPE: PRT
<213> ORGANISM: Homo sapiens

<400> SEQUENCE: 6

```
Met Ala Trp Pro Gly Thr Gly Pro Ser A rg Gly Ala Pro Gly Gly
  1               5                 10                  15

Val Gly Leu Arg Leu Gly Leu Leu Gln P he Leu Leu Leu Leu Arg
             20                  25                  30

Pro Thr Leu Gly Phe Gly Asp Glu Glu A rg Arg Cys Asp Pro Ile
         35                  40                  45

Arg Ile Ala Met Cys Gln Asn Leu Gly Tyr A sn Val Thr Lys Met Pro
     50                  55                  60
```

```
Asn Leu Val Gly His Glu Leu Gln Thr Asp Ala Glu Leu Gln Leu Thr
 65                  70                  75                  80

Thr Phe Thr Pro Leu Ile Gln Tyr Gly Cys Ser Ser Gln Leu Gln Phe
                 85                  90                  95

Phe Leu Cys Ser Val Tyr Val Pro Met Cys Thr Glu Lys Ile Asn Ile
            100                 105                 110

Pro Ile Gly Pro Cys Gly Gly Met Cys Leu Ser Val Lys Arg Arg Cys
            115                 120                 125

Glu Pro Val Leu Arg Glu Phe Gly Phe Ala Trp Pro Asp Thr Leu Asn
    130                 135                 140

Cys Ser Lys Phe Pro Pro Gln Asn Asp His Asn His Met Cys Met Glu
145                 150                 155                 160

Gly Pro Gly Asp Glu Glu Val Pro Leu Pro His Lys Thr Pro Ile Gln
                165                 170                 175

Pro Gly Glu Glu Cys His Ser Val Gly Ser Asn Ser Asp Gln Tyr Ile
            180                 185                 190

Trp Val Lys Arg Ser Leu Asn Cys Val Leu Lys Cys Gly Tyr Asp Ala
        195                 200                 205

Gly Leu Tyr Ser Arg Ser Ala Lys Glu Phe Thr Asp Ile Trp Met Ala
    210                 215                 220

Val Trp Ala Ser Leu Cys Phe Ile Ser Thr Thr Phe Thr Val Leu Thr
225                 230                 235                 240

Phe Leu Ile Asp Ser Ser Arg Phe Ser Tyr Pro Glu Arg Pro Ile Ile
                245                 250                 255

Phe Leu Ser Met Cys Tyr Asn Ile Tyr Ser Ile Ala Tyr Ile Val Arg
            260                 265                 270

Leu Thr Val Gly Arg Glu Arg Ile Ser Cys Asp Phe Glu Glu Ala Ala
        275                 280                 285

Glu Pro Val Leu Ile Gln Glu Gly Leu Lys Asn Thr Gly Cys Ala Ile
    290                 295                 300

Ile Phe Leu Leu Met Tyr Phe Gly Met Ala Ser Ser Ile Trp Trp
305                 310                 315                 320

Val Ile Leu Thr Leu Thr Trp Phe Leu Ala Ala Gly Leu Lys Trp Gly
                325                 330                 335

His Glu Ala Ile Glu Met His Ser Ser Tyr Phe His Ile Ala Ala Trp
            340                 345                 350

Ala Ile Pro Ala Val Lys Thr Ile Val Ile Leu Ile Met Arg Leu Val
        355                 360                 365

Asp Ala Asp Glu Leu Thr Gly Leu Cys Tyr Val Gly Asn Gln Asn Leu
    370                 375                 380

Asp Ala Leu Thr Gly Phe Val Ala Pro Leu Phe Thr Tyr Leu Val
385                 390                 395                 400

Ile Gly Thr Leu Phe Ile Ala Ala Gly Leu Val Ala Leu Phe Lys Ile
                405                 410                 415

Arg Ser Asn Leu Gln Lys Asp Gly Thr Lys Thr Asp Lys Leu Glu Arg
            420                 425                 430

Leu Met Val Lys Ile Gly Val Phe Ser Val Leu Tyr Thr Val Pro Ala
        435                 440                 445

Thr Cys Val Ile Ala Cys Tyr Phe Tyr Glu Ile Ser Asn Trp Ala Leu
450                 455                 460

Phe Arg Tyr Ser Ala Asp Asp Ser Asn Met Ala Val Glu Met Leu Lys
465                 470                 475                 480
```

```
Ile Phe Met Ser Leu Leu Val Gly Ile Thr S er Gly Met Trp Ile Trp
                485                 490                 495

Ser Ala Lys Thr Leu His Thr Trp Gln Lys C ys Ser Asn Arg Leu Val
                500                 505                 510

Asn Ser Gly Lys Val Lys Arg Glu Lys Arg G ly Asn Gly Trp Val Lys
                515                 520                 525

Pro Gly Lys Gly Asn Glu Thr Val Val
                530             535

<210> SEQ ID NO 7
<211> LENGTH: 2260
<212> TYPE: DNA
<213> ORGANISM: Homo sapiens
<220> FEATURE:
<221> NAME/KEY: CDS
<222> LOCATION: (362)...(2077)
<221> NAME/KEY: misc_feature
<222> LOCATION: (1)...(2260)
<223> OTHER INFORMATION: n = A,T,C or G

<400> SEQUENCE: 7
tttgaaggta accggagaag cttgttgctc gtcgccgcag agaaagccgc a ccgttacgt      60 ctcggngggg agggtaaggc gacaccccctt ccctcgtacc cccactccag g cccaggagt    120 ttgaactccg gcggctgcgt gagtgccacg tggaggcggc tgcggcgccc c tcggctggc    180 ggcctcgccc ccgctgtgca ggcaccctag caccctcggc tccgcgccgc c cacggcggc    240 cccggcgccg ggaggactct catgcgcggg ccgggcggcg cgcctccct g tatccaagc     300 ctctccccag cgcctcgtct ttttcctcca gctgagaacg ccgctgcact c gcgaccggc    360 g atg cgg ggc ccc ggc acg gcg gcg tcg cac  tcg ccc ctg ggc ctc tgc     409
  Met Arg Gly Pro Gly Thr Ala Ala Ser His  Ser Pro Leu Gly Leu Cys
    1               5                  10                  15 gcc ctg gtg ctt gct ctt ctg ggc gcg ctg c cc acg gac acc cgg gct        457
Ala Leu Val Leu Ala Leu Leu Gly Ala Leu P ro Thr Asp Thr Arg Ala
                20                  25                  30 cag cca tat cac ggc gag aaa ggc atc tcg g ta ccg gac cac ggc ttc        505
Gln Pro Tyr His Gly Glu Lys Gly Ile Ser V al Pro Asp His Gly Phe
            35                  40                  45 tgc cag ccc atc tcc atc ccg ttg tgc acg g at atc gcc tac aac cag        553
Cys Gln Pro Ile Ser Ile Pro Leu Cys Thr A sp Ile Ala Tyr Asn Gln
        50                  55                  60 acc atc ctg ccc aac ctg ctg ggc cac acg a ac caa gag gac gcg ggc        601
Thr Ile Leu Pro Asn Leu Leu Gly His Thr A sn Gln Glu Asp Ala Gly
 65                  70                  75                  80 ctc gag gtg cac cag ttc tac cct ctg gta a ag gtg cag tgt tct cct        649
Leu Glu Val His Gln Phe Tyr Pro Leu Val L ys Val Gln Cys Ser Pro
                85                  90                  95 gag cta cgc ttc ttc tta tgc tct atg tac g ca ccc gtg tgc acc gtg        697
Glu Leu Arg Phe Phe Leu Cys Ser Met Tyr A la Pro Val Cys Thr Val
            100                 105                 110 ctc gac caa gcc att cct ccg tgc cgt tcc t tg tgc gag cgc gcc cga        745
Leu Asp Gln Ala Ile Pro Pro Cys Arg Ser L eu Cys Glu Arg Ala Arg
        115                 120                 125 cag ggc tgc gag gcg ctc atg aac aag ttc g gc ttc cag tgg cca gag        793
Gln Gly Cys Glu Ala Leu Met Asn Lys Phe G ly Phe Gln Trp Pro Glu
    130                 135                 140 cgg ttg cgc tgc gag aac ttc cca gtg cac g gt gcc ggc gag atc tgc        841
Arg Leu Arg Cys Glu Asn Phe Pro Val His G ly Ala Gly Glu Ile Cys
145                 150                 155                 160 gtg ggg cag aac acg tcc gac ggc tcc ggg g gc gcg ggc ggc agt ccc        889
```

| | | |
|---|---|---|
| Val Gly Gln Asn Thr Ser Asp Gly Ser Gly Ala Gly Gly Ser Pro<br>165                         170                      175 | | |
| acc gcc tac cct act gct ccc tac ctg cca gac cca cct ttc act gcg<br>Thr Ala Tyr Pro Thr Ala Pro Tyr Leu Pro Asp Pro Pro Phe Thr Ala<br>            180                      185                      190 | | 937 |
| atg tcc ccc tca gat ggc aga ggc cgc ttg tct ttc ccc ttc tcg tgt<br>Met Ser Pro Ser Asp Gly Arg Gly Arg Leu Ser Phe Pro Phe Ser Cys<br>            195                      200                      205 | | 985 |
| ccg cgc cag ctc aag gtg ccc ccc tac ctg ggc tac cgc ttc cta ggt<br>Pro Arg Gln Leu Lys Val Pro Pro Tyr Leu Gly Tyr Arg Phe Leu Gly<br>            210                      215                      220 | | 1033 |
| gag cgt gac tgc ggt gcc ccg tgt gag ccg ggc cgt gct aac ggc ctc<br>Glu Arg Asp Cys Gly Ala Pro Cys Glu Pro Gly Arg Ala Asn Gly Leu<br>225                         230                      235                      240 | | 1081 |
| atg tac ttt aaa gaa gag gag aga cgg ttc gcc cgc ctc tgg gtg ggt<br>Met Tyr Phe Lys Glu Glu Glu Arg Arg Phe Ala Arg Leu Trp Val Gly<br>            245                      250                      255 | | 1129 |
| gtg tgg tca gtg ctg tcg tgc gcc tcg acg ctc ttc acg gtg ctc acc<br>Val Trp Ser Val Leu Ser Cys Ala Ser Thr Leu Phe Thr Val Leu Thr<br>            260                      265                      270 | | 1177 |
| tac cta gtg gac atg cgt cgc ttc agc tat cca gag cga ccc atc atc<br>Tyr Leu Val Asp Met Arg Arg Phe Ser Tyr Pro Glu Arg Pro Ile Ile<br>            275                      280                      285 | | 1225 |
| ttc ctg tcg ggt tgc tac ttc atg gtg gca gtg gcg cac gtg gca ggc<br>Phe Leu Ser Gly Cys Tyr Phe Met Val Ala Val Ala His Val Ala Gly<br>            290                      295                      300 | | 1273 |
| ttc ctg cta gag gac cgt gcc gtg tgc gtg gag cgc ttc tcg gac gat<br>Phe Leu Leu Glu Asp Arg Ala Val Cys Val Glu Arg Phe Ser Asp Asp<br>305                       310                      315                      320 | | 1321 |
| ggc tac cgc acg gtg gcg cag ggc acc aag aag gag ggc tgc acc atc<br>Gly Tyr Arg Thr Val Ala Gln Gly Thr Lys Lys Glu Gly Cys Thr Ile<br>            325                      330                      335 | | 1369 |
| ctc ttc atg gtg ctt tac ttc ttc ggt atg gcc agc tcc atc tgg tgg<br>Leu Phe Met Val Leu Tyr Phe Phe Gly Met Ala Ser Ser Ile Trp Trp<br>            340                      345                      350 | | 1417 |
| gtc att ctg tcc ctc act tgg ttc ctg gca gct ggc atg aag tgg ggc<br>Val Ile Leu Ser Leu Thr Trp Phe Leu Ala Ala Gly Met Lys Trp Gly<br>            355                      360                      365 | | 1465 |
| cac gag gcc atc gag gcc aac tcg cag tac ttt cat ctg gcc gcg tgg<br>His Glu Ala Ile Glu Ala Asn Ser Gln Tyr Phe His Leu Ala Ala Trp<br>            370                      375                      380 | | 1513 |
| gct gtg cca gcg gtc aag aca atc acc att ttg gcc atg ggc cag gtg<br>Ala Val Pro Ala Val Lys Thr Ile Thr Ile Leu Ala Met Gly Gln Val<br>385                       390                      395                      400 | | 1561 |
| gat ggt gac cta ctc agt gga gtg tgc tac gtg ggc ctg tct agt gtg<br>Asp Gly Asp Leu Leu Ser Gly Val Cys Tyr Val Gly Leu Ser Ser Val<br>            405                      410                      415 | | 1609 |
| gat gca ttg cgg ggc ttc gtg ctg gcg ccc ttg ttc gtc tac ctc ttc<br>Asp Ala Leu Arg Gly Phe Val Leu Ala Pro Leu Phe Val Tyr Leu Phe<br>            420                      425                      430 | | 1657 |
| atc ggg acg tcc ttc ctg ttg gcc ggc ttt gtg tct ctc ttt cgc atc<br>Ile Gly Thr Ser Phe Leu Leu Ala Gly Phe Val Ser Leu Phe Arg Ile<br>            435                      440                      445 | | 1705 |
| cgc acc atc atg aag cac gac ggc acc aag aca gag aag ctg gag aag<br>Arg Thr Ile Met Lys His Asp Gly Thr Lys Thr Glu Lys Leu Glu Lys<br>            450                      455                      460 | | 1753 |
| ctg atg gtg cgc atc ggc gtc ttc agc gtg ctc tac acg gtg ccg gcc<br>Leu Met Val Arg Ile Gly Val Phe Ser Val Leu Tyr Thr Val Pro Ala<br>465                       470                      475                      480 | | 1801 |

```
acc atc gtg ttg gcc tgc tac ttt tat gag c ag gcc ttc cga gag cac      1849
Thr Ile Val Leu Ala Cys Tyr Phe Tyr Glu G ln Ala Phe Arg Glu His
            485                 490                 495 tgg gaa cgc acc tgg ctc ctg cag act tgc a ag agc tac gct gtg ccc      1897
Trp Glu Arg Thr Trp Leu Leu Gln Thr Cys L ys Ser Tyr Ala Val Pro
        500                 505                 510 tgc cct ccg cgc cac ttc tct ccc atg agc c cc gac ttt aca gtc ttc      1945
Cys Pro Pro Arg His Phe Ser Pro Met Ser P ro Asp Phe Thr Val Phe
    515                 520                 525 atg atc aag tac ctg atg acc atg atc gtg g gc atc act acg ggc ttc      1993
Met Ile Lys Tyr Leu Met Thr Met Ile Val G ly Ile Thr Thr Gly Phe
530                 535                 540 tgg atc tgg tcg ggc aag acc ctg cag tca t gg cgt cgc ttc tac cac      2041
Trp Ile Trp Ser Gly Lys Thr Leu Gln Ser T rp Arg Arg Phe Tyr His
545                 550                 555                 560 aga ctc agc cac agc agc aag ggg gaa act g cg gta tgagccccgg           2087
Arg Leu Ser His Ser Ser Lys Gly Glu Thr A la Val
                565                 570 tccttaccca cccttgcctc ttctacccctt ttacaggagg agaggcatgg t agggagaga   2147 actgctgggt gggggcttgt ttccgtaagc tacctgcccc ctccactgag c tttaacctg   2207 gaagtgagaa gttatttgga ggtgagaaga gatttggggg cgagagatgg t tt          2260

<210> SEQ ID NO 8
<211> LENGTH: 572
<212> TYPE: PRT
<213> ORGANISM: Homo sapiens

<400> SEQUENCE: 8

Met Arg Gly Pro Gly Thr Ala Ala Ser His S er Pro Leu Gly Leu Cys
1               5                   10                  15

Ala Leu Val Leu Ala Leu Leu Gly Ala Leu P ro Thr Asp Thr Arg Ala
            20                  25                  30

Gln Pro Tyr His Gly Glu Lys Gly Ile Ser V al Pro Asp His Gly Phe
        35                  40                  45

Cys Gln Pro Ile Ser Ile Pro Leu Cys Thr A sp Ile Ala Tyr Asn Gln
    50                  55                  60

Thr Ile Leu Pro Asn Leu Leu Gly His Thr A sn Gln Glu Asp Ala Gly
65                  70                  75                  80

Leu Glu Val His Gln Phe Tyr Pro Leu Val L ys Val Gln Cys Ser Pro
                85                  90                  95

Glu Leu Arg Phe Phe Leu Cys Ser Met Tyr A la Pro Val Cys Thr Val
            100                 105                 110

Leu Asp Gln Ala Ile Pro Pro Cys Arg Ser L eu Cys Glu Arg Ala Arg
        115                 120                 125

Gln Gly Cys Glu Ala Leu Met Asn Lys Phe G ly Phe Gln Trp Pro Glu
    130                 135                 140

Arg Leu Arg Cys Glu Asn Phe Pro Val His G ly Ala Gly Glu Ile Cys
145                 150                 155                 160

Val Gly Gln Asn Thr Ser Asp Gly Ser Gly G ly Ala Gly Gly Ser Pro
                165                 170                 175

Thr Ala Tyr Pro Thr Ala Pro Tyr Leu Pro A sp Pro Pro Phe Thr Ala
            180                 185                 190

Met Ser Pro Ser Asp Gly Arg Gly Arg Leu S er Phe Pro Phe Ser Cys
        195                 200                 205

Pro Arg Gln Leu Lys Val Pro Pro Tyr Leu G ly Tyr Arg Phe Leu Gly
    210                 215                 220
```

```
Glu Arg Asp Cys Gly Ala Pro Cys Glu Pro Gly Arg Ala Asn Gly Leu
225                 230                 235                 240

Met Tyr Phe Lys Glu Glu Arg Arg Phe Ala Arg Leu Trp Val Gly
            245                 250                 255

Val Trp Ser Val Leu Ser Cys Ala Ser Thr Leu Phe Thr Val Leu Thr
        260                 265                 270

Tyr Leu Val Asp Met Arg Arg Phe Ser Tyr Pro Glu Arg Pro Ile Ile
    275                 280                 285

Phe Leu Ser Gly Cys Tyr Phe Met Val Ala Val Ala His Val Ala Gly
        290                 295                 300

Phe Leu Leu Glu Asp Arg Ala Val Cys Val Glu Arg Phe Ser Asp Asp
305                 310                 315                 320

Gly Tyr Arg Thr Val Ala Gln Gly Thr Lys Lys Glu Gly Cys Thr Ile
                325                 330                 335

Leu Phe Met Val Leu Tyr Phe Phe Gly Met Ala Ser Ser Ile Trp Trp
            340                 345                 350

Val Ile Leu Ser Leu Thr Trp Phe Leu Ala Ala Gly Met Lys Trp Gly
        355                 360                 365

His Glu Ala Ile Glu Ala Asn Ser Gln Tyr Phe His Leu Ala Ala Trp
    370                 375                 380

Ala Val Pro Ala Val Lys Thr Ile Thr Ile Leu Ala Met Gly Gln Val
385                 390                 395                 400

Asp Gly Asp Leu Leu Ser Gly Val Cys Tyr Val Gly Leu Ser Ser Val
                405                 410                 415

Asp Ala Leu Arg Gly Phe Val Leu Ala Pro Leu Phe Val Tyr Leu Phe
            420                 425                 430

Ile Gly Thr Ser Phe Leu Leu Ala Gly Phe Val Ser Leu Phe Arg Ile
        435                 440                 445

Arg Thr Ile Met Lys His Asp Gly Thr Lys Thr Glu Lys Leu Glu Lys
    450                 455                 460

Leu Met Val Arg Ile Gly Val Phe Ser Val Leu Tyr Thr Val Pro Ala
465                 470                 475                 480

Thr Ile Val Leu Ala Cys Tyr Phe Tyr Glu Gln Ala Phe Arg Glu His
                485                 490                 495

Trp Glu Arg Thr Trp Leu Leu Gln Thr Cys Lys Ser Tyr Ala Val Pro
            500                 505                 510

Cys Pro Pro Arg His Phe Ser Pro Met Ser Pro Asp Phe Thr Val Phe
        515                 520                 525

Met Ile Lys Tyr Leu Met Thr Met Ile Val Gly Ile Thr Thr Gly Phe
    530                 535                 540

Trp Ile Trp Ser Gly Lys Thr Leu Gln Ser Trp Arg Arg Phe Tyr His
545                 550                 555                 560

Arg Leu Ser His Ser Ser Lys Gly Glu Thr Ala Val
                565                 570

<210> SEQ ID NO 9
<211> LENGTH: 2421
<212> TYPE: DNA
<213> ORGANISM: Homo sapiens
<220> FEATURE:
<221> NAME/KEY: CDS
<222> LOCATION: (188)...(2242)

<400> SEQUENCE: 9
gggggagggc cggacgactc cagcctaggt ttccaaccct gctgcctgaa aaggagatag    60
```

-continued

```
actgttgcta ttctcctctg cagagaaaag tgggacacga cccgctctcc c ttttctcag       120 attcctcact gcagagccct cctgcgcgcc gcctagagaa ggaggacttg g ggtcccagc       180 gcgcagc atg gag tgg ggt tac ctg ttg gaa gtg acc tcg ctc cta gcc         229
        Met Glu Trp Gly Tyr Leu Leu Glu Val Thr Ser Leu Leu Ala
         1               5                   10 gcc ttg gcg gtg cta cag cgc tct agc ggc g ct gcc gcg gct tcg gcc       277
Ala Leu Ala Val Leu Gln Arg Ser Ser Gly A la Ala Ala Ala Ser Ala
 15                  20                  25                  30 aag gag ctg gcg tgc caa gag atc acg gtg c cg ttg tgc aaa ggc atc       325
Lys Glu Leu Ala Cys Gln Glu Ile Thr Val P ro Leu Cys Lys Gly Ile
                 35                  40                  45 ggt tac aac tac act tac atg ccc aac cag t tc aac cac gac acg caa       373
Gly Tyr Asn Tyr Thr Tyr Met Pro Asn Gln P he Asn His Asp Thr Gln
             50                  55                  60 gat gag gcg ggc cta gag gtg cac cag ttt t gg ccg ctg gtg gag ata       421
Asp Glu Ala Gly Leu Glu Val His Gln Phe T rp Pro Leu Val Glu Ile
         65                  70                  75 cag tgc tcc ccg gac ctc aag ttc ttt ctg t gt agc atg tac acg ccc       469
Gln Cys Ser Pro Asp Leu Lys Phe Phe Leu C ys Ser Met Tyr Thr Pro
     80                  85                  90 atc tgc ctg gag gac tac aag aag cct ctg c cg cct tgt cgc tct gtg       517
Ile Cys Leu Glu Asp Tyr Lys Lys Pro Leu P ro Pro Cys Arg Ser Val
 95                 100                 105                 110 tgt gaa cgc gcc aag gcc ggc tgc gcg ccg c tc atg cgc cag tac ggc       565
Cys Glu Arg Ala Lys Ala Gly Cys Ala Pro L eu Met Arg Gln Tyr Gly
                115                 120                 125 ttt gct tgg cct gac cgc atg cgc tgc gat c gg ttg ccg gag cag ggc       613
Phe Ala Trp Pro Asp Arg Met Arg Cys Asp A rg Leu Pro Glu Gln Gly
            130                 135                 140 aac ccg gac act ctg tgc atg gac tac aac c gc acc gac ctc acc acg       661
Asn Pro Asp Thr Leu Cys Met Asp Tyr Asn A rg Thr Asp Leu Thr Thr
        145                 150                 155 gcc gcg ccc agc cca ccg cgc cgc ctg cct c cg ccg cct cct ccc ggc       709
Ala Ala Pro Ser Pro Pro Arg Arg Leu Pro P ro Pro Pro Pro Pro Gly
    160                 165                 170 gag cag ccg ccc tct ggc agc ggc cac agc c gc ccg cca ggg gcc agg       757
Glu Gln Pro Pro Ser Gly Ser Gly His Ser A rg Pro Pro Gly Ala Arg
175                 180                 185                 190 ccc cca cat cgt ggc ggc agc agt agg ggc a gc ggg gac gcg gcg gct       805
Pro Pro His Arg Gly Gly Ser Ser Arg Gly S er Gly Asp Ala Ala Ala
                195                 200                 205 gcg ccc cct tcg cgc ggc ggg aag gcg agg c cc cct ggt ggc ggc gct       853
Ala Pro Pro Ser Arg Gly Gly Lys Ala Arg P ro Pro Gly Gly Gly Ala
            210                 215                 220 gct ccc tgc gag ccg ggg tgc cag tgc cgc g cg ccc atg gtg agc gtg       901
Ala Pro Cys Glu Pro Gly Cys Gln Cys Arg A la Pro Met Val Ser Val
        225                 230                 235 tcc agc gaa cgc cac ccg ctc tac aac cgc g tc aag acc ggc cag atc       949
Ser Ser Glu Arg His Pro Leu Tyr Asn Arg V al Lys Thr Gly Gln Ile
    240                 245                 250 gcc aac tgt gcg ctg ccc tgc cac aac ccc t tc ttt agc cag gat gag       997
Ala Asn Cys Ala Leu Pro Cys His Asn Pro P he Phe Ser Gln Asp Glu
255                 260                 265                 270 cgc gcc ttc acc gtc ttc tgg atc ggc ctg t gg tcg gtg ctc tgc ttc      1045
Arg Ala Phe Thr Val Phe Trp Ile Gly Leu T rp Ser Val Leu Cys Phe
                275                 280                 285
```

-continued

```
gtc tcc acc ttc gcc act gtc tct acc ttc c tc atc gat atg gag cgc      1093
Val Ser Thr Phe Ala Thr Val Ser Thr Phe L eu Ile Asp Met Glu Arg
            290                 295                 300 ttt aag tac ccg gaa cgg ccc atc ata ttc c tc tcc gcc tgt tac ctc      1141
Phe Lys Tyr Pro Glu Arg Pro Ile Ile Phe L eu Ser Ala Cys Tyr Leu
            305                 310                 315 ttc gtg tct gtc ggg tac ctg gtg cgc ctg g tg gca gga cat gag aaa      1189
Phe Val Ser Val Gly Tyr Leu Val Arg Leu V al Ala Gly His Glu Lys
            320                 325                 330 gtg gcc tgc agc ggc ggc gct ccg ggt gct g gc gga cgt ggg ggt gcg      1237
Val Ala Cys Ser Gly Gly Ala Pro Gly Ala G ly Gly Arg Gly Gly Ala
335                 340                 345                 350 ggc ggc gcg gcg gcg gct ggc gca ggg gca g cg gga cgg ggg gcg agc      1285
Gly Gly Ala Ala Ala Gly Ala Gly Ala A la Gly Arg Gly Ala Ser
                355                 360                 365 agc ccg ggc gcg cgc ggc gag tac gag gag c tg ggc gca gtt gag cag      1333
Ser Pro Gly Ala Arg Gly Glu Tyr Glu Glu L eu Gly Ala Val Glu Gln
            370                 375                 380 cat gtt cgc tat gag acc act ggc ccc gcg c tg tgc acg gtg gtc ttt      1381
His Val Arg Tyr Glu Thr Thr Gly Pro Ala L eu Cys Thr Val Val Phe
            385                 390                 395 ctc ctt gtc tac ttt ttt ggc atg gcc agc t cc atc tgg tgg gta atc      1429
Leu Leu Val Tyr Phe Phe Gly Met Ala Ser S er Ile Trp Trp Val Ile
            400                 405                 410 ctg tcg ctc acg tgg ttc ttg gca gct ggc a tg aag tgg ggt aac gag      1477
Leu Ser Leu Thr Trp Phe Leu Ala Ala Gly M et Lys Trp Gly Asn Glu
415                 420                 425                 430 gcc ata gca ggc tac tcg cag tac ttc cac c tg gcc gcg tgg ctt gtg      1525
Ala Ile Ala Gly Tyr Ser Gln Tyr Phe His L eu Ala Ala Trp Leu Val
                435                 440                 445 ccc agc gtc aag tcc atc gcg gtg ctg gcg c tc agc tcc gta gac ggc      1573
Pro Ser Val Lys Ser Ile Ala Val Leu Ala L eu Ser Ser Val Asp Gly
            450                 455                 460 gac ccg gtg gcg ggc atc tgc tac gtg ggc a ac cag agc ctt gac aac      1621
Asp Pro Val Ala Gly Ile Cys Tyr Val Gly A sn Gln Ser Leu Asp Asn
            465                 470                 475 cta cgc ggc ttt gtg ctg gcg cca ctg gtt a tc tac ctc ttc att ggg      1669
Leu Arg Gly Phe Val Leu Ala Pro Leu Val I le Tyr Leu Phe Ile Gly
            480                 485                 490 act atg ttt ctg tta gct ggc ttc gtg tcg c tg ttc cga atc cgt tca      1717
Thr Met Phe Leu Leu Ala Gly Phe Val Ser L eu Phe Arg Ile Arg Ser
495                 500                 505                 510 gtc atc aag cag caa gga ggt cca act aag a ca cac aag cta gaa aaa      1765
Val Ile Lys Gln Gln Gly Gly Pro Thr Lys T hr His Lys Leu Glu Lys
                515                 520                 525 ctc atg atc cgc ttg ggc ctc ttc acc gtg c tc tac acg gtg ccc gct      1813
Leu Met Ile Arg Leu Gly Leu Phe Thr Val L eu Tyr Thr Val Pro Ala
            530                 535                 540 gcc gtc gtt gtc gcc tgc ctt ttc tat gag c ag cac aac cga ccg cgc      1861
Ala Val Val Val Ala Cys Leu Phe Tyr Glu G ln His Asn Arg Pro Arg
            545                 550                 555 tgg gag gcc acg cac aac tgc cca tgc ctt c gg gac ctg caa ccg gac      1909
Trp Glu Ala Thr His Asn Cys Pro Cys Leu A rg Asp Leu Gln Pro Asp
            560                 565                 570 cag gct cgc agg ccc gat tac gcg gtc ttc a tg ctc aag tac ttc atg      1957
Gln Ala Arg Arg Pro Asp Tyr Ala Val Phe M et Leu Lys Tyr Phe Met
575                 580                 585                 590
```

```
tgc cta gta gtg ggc atc aca tcg ggc gtg t gg gtc tgg tcc ggc aag    2005
Cys Leu Val Val Gly Ile Thr Ser Gly Val T rp Val Trp Ser Gly Lys
                595                 600                 605 act ctg gag tcc tgg cgc gcg ttg tgc act a gg tgc tgc tgg gcc agc    2053
Thr Leu Glu Ser Trp Arg Ala Leu Cys Thr A rg Cys Cys Trp Ala Ser
            610                 615                 620 aag ggc gct gca gta ggc gcg ggc gct gga g gc agc ggc cct ggg ggc    2101
Lys Gly Ala Ala Val Gly Ala Gly Ala Gly S er Gly Pro Gly Gly
                625                 630                 635 agt gga ccc ggg ccc ggc gga ggt ggg gga c ac ggc gga ggc ggg gga    2149
Ser Gly Pro Gly Pro Gly Gly Gly Gly H is Gly Gly Gly Gly
                640                 645                 650 tcc ctc tac agc gac gtc agt acc ggc ctg a cg tgg cgg tct ggc acg    2197
Ser Leu Tyr Ser Asp Val Ser Thr Gly Leu T hr Trp Arg Ser Gly Thr
655                 660                 665                 670 gcc agc tct gta tct tac cct aag caa atg c ca ttg tcc cag gtc        2242
Ala Ser Ser Val Ser Tyr Pro Lys Gln Met P ro Leu Ser Gln Val
                    675                 680                 685 tgaaccctac gtggatgccc agaaggggcg gagaggagtg ggggatgggg a acccgtggg    2302 cggcgaaggg accccagacc ggccagggtt cccacccctt cccagtgttg a ctgctatag   2362 catgacaatg aagtgttaat ggtatccatt agcagcgggg acttaaatga c tcccttag    2421

<210> SEQ ID NO 10
<211> LENGTH: 685
<212> TYPE: PRT
<213> ORGANISM: Homo sapiens

<400> SEQUENCE: 10

Met Glu Trp Gly Tyr Leu Leu Glu Val Thr S er Leu Leu Ala Ala Leu
1               5                   10                  15

Ala Val Leu Gln Arg Ser Ser Gly Ala Ala A la Ala Ser Ala Lys Glu
            20                  25                  30

Leu Ala Cys Gln Glu Ile Thr Val Pro Leu C ys Lys Gly Ile Gly Tyr
        35                  40                  45

Asn Tyr Thr Tyr Met Pro Asn Gln Phe Asn H is Asp Thr Gln Asp Glu
    50                  55                  60

Ala Gly Leu Glu Val His Gln Phe Trp Pro L eu Val Glu Ile Gln Cys
65                  70                  75                  80

Ser Pro Asp Leu Lys Phe Phe Leu Cys Ser M et Tyr Thr Pro Ile Cys
                85                  90                  95

Leu Glu Asp Tyr Lys Lys Pro Leu Pro Pro C ys Arg Ser Val Cys Glu
            100                 105                 110

Arg Ala Lys Ala Gly Cys Ala Pro Leu Met A rg Gln Tyr Gly Phe Ala
        115                 120                 125

Trp Pro Asp Arg Met Arg Cys Asp Arg Leu P ro Glu Gln Gly Asn Pro
    130                 135                 140

Asp Thr Leu Cys Met Asp Tyr Asn Arg Thr A sp Leu Thr Thr Ala Ala
145                 150                 155                 160

Pro Ser Pro Pro Arg Arg Leu Pro Pro Pro P ro Pro Pro Gly Glu Gln
                165                 170                 175

Pro Pro Ser Gly Ser Gly His Ser Arg Pro P ro Gly Ala Arg Pro Pro
            180                 185                 190

His Arg Gly Gly Ser Ser Arg Gly Ser Gly A sp Ala Ala Ala Ala Pro
        195                 200                 205
```

-continued

```
Pro Ser Arg Gly Gly Lys Ala Arg Pro Gly Gly Gly Ala Ala Pro
    210                 215                 220
Cys Glu Pro Gly Cys Gln Cys Arg Ala Pro Met Val Ser Val Ser Ser
225                 230                 235                 240
Glu Arg His Pro Leu Tyr Asn Arg Val Lys Thr Gly Gln Ile Ala Asn
                245                 250                 255
Cys Ala Leu Pro Cys His Asn Pro Phe Phe Ser Gln Asp Glu Arg Ala
                260                 265                 270
Phe Thr Val Phe Trp Ile Gly Leu Trp Ser Val Leu Cys Phe Val Ser
                275                 280                 285
Thr Phe Ala Thr Val Ser Thr Phe Leu Ile Asp Met Glu Arg Phe Lys
    290                 295                 300
Tyr Pro Glu Arg Pro Ile Ile Phe Leu Ser Ala Cys Tyr Leu Phe Val
305                 310                 315                 320
Ser Val Gly Tyr Leu Val Arg Leu Val Ala Gly His Glu Lys Val Ala
                325                 330                 335
Cys Ser Gly Gly Ala Pro Gly Ala Gly Gly Arg Gly Gly Ala Gly Gly
                340                 345                 350
Ala Ala Ala Ala Gly Ala Gly Ala Ala Gly Arg Gly Ala Ser Ser Pro
                355                 360                 365
Gly Ala Arg Gly Glu Tyr Glu Glu Leu Gly Ala Val Glu Gln His Val
    370                 375                 380
Arg Tyr Glu Thr Thr Gly Pro Ala Leu Cys Thr Val Val Phe Leu Leu
385                 390                 395                 400
Val Tyr Phe Phe Gly Met Ala Ser Ser Ile Trp Trp Val Ile Leu Ser
                405                 410                 415
Leu Thr Trp Phe Leu Ala Ala Gly Met Lys Trp Gly Asn Glu Ala Ile
                420                 425                 430
Ala Gly Tyr Ser Gln Tyr Phe His Leu Ala Ala Trp Leu Val Pro Ser
                435                 440                 445
Val Lys Ser Ile Ala Val Leu Ala Leu Ser Ser Val Asp Gly Asp Pro
    450                 455                 460
Val Ala Gly Ile Cys Tyr Val Gly Asn Gln Ser Leu Asp Asn Leu Arg
465                 470                 475                 480
Gly Phe Val Leu Ala Pro Leu Val Ile Tyr Leu Phe Ile Gly Thr Met
                485                 490                 495
Phe Leu Leu Ala Gly Phe Val Ser Leu Phe Arg Ile Arg Ser Val Ile
                500                 505                 510
Lys Gln Gln Gly Gly Pro Thr Lys Thr His Lys Leu Glu Lys Leu Met
                515                 520                 525
Ile Arg Leu Gly Leu Phe Thr Val Leu Tyr Thr Val Pro Ala Ala Val
    530                 535                 540
Val Val Ala Cys Leu Phe Tyr Glu Gln His Asn Arg Pro Arg Trp Glu
545                 550                 555                 560
Ala Thr His Asn Cys Pro Cys Leu Arg Asp Leu Gln Pro Asp Gln Ala
                565                 570                 575
Arg Arg Pro Asp Tyr Ala Val Phe Met Leu Lys Tyr Phe Met Cys Leu
                580                 585                 590
Val Val Gly Ile Thr Ser Gly Val Trp Val Trp Ser Gly Lys Thr Leu
                595                 600                 605
Glu Ser Trp Arg Ala Leu Cys Thr Arg Cys Cys Trp Ala Ser Lys Gly
    610                 615                 620
```

```
Ala Ala Val Gly Ala Gly Ala Gly Gly Ser G ly Pro Gly Gly Ser Gly
625                 630                 635                 640

Pro Gly Pro Gly Gly Gly Gly His Gly G ly Gly Gly Gly Ser Leu
            645                 650                 655

Tyr Ser Asp Val Ser Thr Gly Leu Thr Trp A rg Ser Gly Thr Ala Ser
            660                 665                 670

Ser Val Ser Tyr Pro Lys Gln Met Pro Leu S er Gln Val
            675                 680                 685

<210> SEQ ID NO 11
<211> LENGTH: 1909
<212> TYPE: DNA
<213> ORGANISM: Homo sapiens
<220> FEATURE:
<221> NAME/KEY: CDS
<222> LOCATION: (70)...(1044)
<221> NAME/KEY: misc_feature
<222> LOCATION: (1)...(1909)
<223> OTHER INFORMATION: n = A,T,C or G

<400> SEQUENCE: 11
cggagacggc ggagcgggcc ttgttggcgt ccactgcgcg gntgcaccct g cccatcct        60 gccgggatc atg gtc tgc ggc agc ccg gga ggg at g ctg ctg ctg cgg gcc     111
          Met Val Cys Gly Ser  Pro Gly Gly Met Leu Leu Leu Arg Ala
            1               5                 10 ggg ctg ctt gcc ctg gct gct ctc tgc ctg c tc cgg gtg ccc ggg gct      159
Gly Leu Leu Ala Leu Ala Ala Leu Cys Leu L eu Arg Val Pro Gly Ala
 15                  20                  25                  30 cgg gct gca gcc tgt gag ccc gtc cgc atc c cc ctg tgc aag tcc ctg      207
Arg Ala Ala Ala Cys Glu Pro Val Arg Ile P ro Leu Cys Lys Ser Leu
                 35                  40                  45 ccc tgg aac atg act aag atg ccc aac cac c tg cac cac agc act cag      255
Pro Trp Asn Met Thr Lys Met Pro Asn His L eu His His Ser Thr Gln
             50                  55                  60 gac aac gcc atc ctg gcc atc gag cag ttc g aa ggt ctg ctg ggc acc      303
Asp Asn Ala Ile Leu Ala Ile Glu Gln Phe G lu Gly Leu Leu Gly Thr
         65                  70                  75 cac tgc agc ccc gat ctg ctc ttc ttc ctc t gt gcc atg tac gcg ccc      351
His Cys Ser Pro Asp Leu Leu Phe Phe Leu C ys Ala Met Tyr Ala Pro
     80                  85                  90 atc tgc acc att gac ttc cag cac gag ccc a tc aag ccc tgt aag tct      399
Ile Cys Thr Ile Asp Phe Gln His Glu Pro I le Lys Pro Cys Lys Ser
 95                 100                 105                 110 gtg tgc gag cgg gcc cgg cag ggc tgt gag c cc ata ctc atc aag tac      447
Val Cys Glu Arg Ala Arg Gln Gly Cys Glu P ro Ile Leu Ile Lys Tyr
                115                 120                 125 cgc cac tcg tgg ccg gag aac ctg gcc tgc g ag gag ctg cca gtg tac      495
Arg His Ser Trp Pro Glu Asn Leu Ala Cys G lu Glu Leu Pro Val Tyr
            130                 135                 140 gac agg ggc gtg tgc atc tct ccc gag gcc a tc gtt act gcg gac gga      543
Asp Arg Gly Val Cys Ile Ser Pro Glu Ala I le Val Thr Ala Asp Gly
        145                 150                 155 gct gat ttt cct atg gat tct agt aac gga a ac tgt aga ggg gca agc      591
Ala Asp Phe Pro Met Asp Ser Ser Asn Gly A sn Cys Arg Gly Ala Ser
    160                 165                 170 agt gaa cgc tgt aaa tgt aag cct att aga g ct aca cag aag acc tat      639
Ser Glu Arg Cys Lys Cys Lys Pro Ile Arg A la Thr Gln Lys Thr Tyr
175                 180                 185                 190 ttc cgg aac aat tac aac tat gtc att cgg g ct aaa gtt aaa gag ata      687
Phe Arg Asn Asn Tyr Asn Tyr Val Ile Arg A la Lys Val Lys Glu Ile
                195                 200                 205
```

```
aag act aag tgc cat gat gtg act gca gta g tg gag gtg aag gag att      735
Lys Thr Lys Cys His Asp Val Thr Ala Val V al Glu Val Lys Glu Ile
                210                 215                 220 cta aag tcc tct ctg gta aac att cca cgg g ac act gtc aac ctc tat      783
Leu Lys Ser Ser Leu Val Asn Ile Pro Arg A sp Thr Val Asn Leu Tyr
                225                 230                 235 acc agc tct ggc tgc ctc tgc cct cca ctt a at gtt aat gag gaa tat      831
Thr Ser Ser Gly Cys Leu Cys Pro Pro Leu A sn Val Asn Glu Glu Tyr
            240                 245                 250 atc atc atg ggc tat gaa gat gag gaa cgt t cc aga tta ctc ttg gtg      879
Ile Ile Met Gly Tyr Glu Asp Glu Glu Arg S er Arg Leu Leu Leu Val
255                 260                 265                 270 gaa ggc tct ata gct gag aag tgg aag gat c ga ctc ggt aaa aaa gtt     927
Glu Gly Ser Ile Ala Glu Lys Trp Lys Asp A rg Leu Gly Lys Lys Val
                275                 280                 285 aag cgc tgg gat atg aag ctt cgt cat ctt g ga ctc agt aaa agt gat     975
Lys Arg Trp Asp Met Lys Leu Arg His Leu G ly Leu Ser Lys Ser Asp
                290                 295                 300 tct agc aat agt gat tcc act cag agt cag a ag tct ggc agg aac tcg   1023
Ser Ser Asn Ser Asp Ser Thr Gln Ser Gln L ys Ser Gly Arg Asn Ser
305                 310                 315 aac ccc cgg caa gca cgc aac taaatcccga aatacaaa aa gtaacacagt      1074
Asn Pro Arg Gln Ala Arg Asn
        320                 325 ggacttccta ttaagactta cttgcattgc tggactagca aaggaaaatt g cactattgc   1134 acatcatatt ctattgttta ctataaaaat catgtgataa ctgattatta c ttctgtttc   1194 tcttttggtt tctgcttctc tcttctctca accccttttgt aatggtttgg g ggcagactc  1254 ttaagtatat tgtgagtttt ctatttcact aatcatgaga aaaactgttc t tttgcaata  1314 ataataaatt aaacatgctg ttaccagagc ctctttgctg gagtctccag a tgttaattt   1374 actttctgca ccccaattgg gaatgcaata ttggatgaaa agagaggttt c tggtattca  1434 cagaaagcta gatatgcctt aaaacatact ctgccgatct aattacagcc t tattttgt    1494 atgccttttg ggcattctcc tcatgcttag aaagttccaa atgtttataa a ggtaaaatg  1554 gcagtttgaa gtcaaatgtc acataggcaa agcaatcaag caccaggaag t gtttatgag  1614 gaaacaacac ccaagatgaa ttatttttga gactgtcagg aagtaaaata a ataggagct  1674 taagaaagaa cattttgcct gattgagaag cacaactgaa accagtagcc g ctggggtgt  1734 taatggtagc attcttcttt tggcaataca tttgatttgt tcatgaatat a ttaatcagc  1794 attagagaaa tgaattataa ctagacatct gctgttatca ccatagtttt g tttaatttg  1854 cttccttta aataaaccca ttggtgaaag tcccaaaaaa aaaaaaaaa a aaaa        1909
```

<210> SEQ ID NO 12
<211> LENGTH: 325
<212> TYPE: PRT
<213> ORGANISM: Homo sapiens

<400> SEQUENCE: 12

Met Val Cys Gly Ser Pro Gly Gly Met Leu L eu Leu Arg Ala Gly Leu
1               5                   10                  15

Leu Ala Leu Ala Ala Leu Cys Leu Leu Arg V al Pro Gly Ala Arg Ala
                20                  25                  30

Ala Ala Cys Glu Pro Val Arg Ile Pro Leu C ys Lys Ser Leu Pro Trp
            35                  40                  45

-continued

```
Asn Met Thr Lys Met Pro Asn His Leu His His Ser Thr Gln Asp Asn
 50                  55                  60
Ala Ile Leu Ala Ile Glu Gln Phe Glu Gly Leu Leu Gly Thr His Cys
 65                  70                  75                  80
Ser Pro Asp Leu Leu Phe Phe Leu Cys Ala Met Tyr Ala Pro Ile Cys
                 85                  90                  95
Thr Ile Asp Phe Gln His Glu Pro Ile Lys Pro Cys Lys Ser Val Cys
                100                 105                 110
Glu Arg Ala Arg Gln Gly Cys Glu Pro Ile Leu Ile Lys Tyr Arg His
            115                 120                 125
Ser Trp Pro Glu Asn Leu Ala Cys Glu Leu Pro Val Tyr Asp Arg
130                 135                 140
Gly Val Cys Ile Ser Pro Glu Ala Ile Val Thr Ala Asp Gly Ala Asp
145                 150                 155                 160
Phe Pro Met Asp Ser Ser Asn Gly Asn Cys Arg Gly Ala Ser Ser Glu
                165                 170                 175
Arg Cys Lys Cys Lys Pro Ile Arg Ala Thr Gln Lys Thr Tyr Phe Arg
                180                 185                 190
Asn Asn Tyr Asn Tyr Val Ile Arg Ala Lys Val Lys Glu Ile Lys Thr
            195                 200                 205
Lys Cys His Asp Val Thr Ala Val Val Glu Val Lys Glu Ile Leu Lys
        210                 215                 220
Ser Ser Leu Val Asn Ile Pro Arg Asp Thr Val Asn Leu Tyr Thr Ser
225                 230                 235                 240
Ser Gly Cys Leu Cys Pro Pro Leu Asn Val Asn Glu Glu Tyr Ile Ile
                245                 250                 255
Met Gly Tyr Glu Asp Glu Glu Arg Ser Arg Leu Leu Leu Val Glu Gly
                260                 265                 270
Ser Ile Ala Glu Lys Trp Lys Asp Arg Leu Gly Lys Lys Val Lys Arg
            275                 280                 285
Trp Asp Met Lys Leu Arg His Leu Gly Leu Ser Lys Ser Asp Ser Ser
        290                 295                 300
Asn Ser Asp Ser Thr Gln Ser Gln Lys Ser Gly Arg Asn Ser Asn Pro
305                 310                 315                 320
Arg Gln Ala Arg Asn
            325

<210> SEQ ID NO 13
<211> LENGTH: 1076
<212> TYPE: DNA
<213> ORGANISM: Homo sapiens
<220> FEATURE:
<221> NAME/KEY: CDS
<222> LOCATION: (2)...(785)
<221> NAME/KEY: misc_feature
<222> LOCATION: (1)...(1076)
<223> OTHER INFORMATION: n = A,T,C or G

<400> SEQUENCE: 13 g gct aac ncc atc ctg ncn atc gan caa ttc  gaa ggt ctg ctg gnc acc     49
  Ala Asn Xaa Ile Leu Xaa Ile Xaa Gln Phe Glu Gly Leu Leu Xaa Thr
  1               5                  10                  15 cac tgc ann ggg gat ctg ctc ttc ttc ctc t gc gcn atg tat gca ccc        97
His Cys Xaa Gly Asp Leu Leu Phe Phe Leu Cys Xaa Met Tyr Ala Pro
            20                  25                  30
```

```
atc tgc acc ntc gac ttc cag cgg gaa ccc a tc aag ccc tgc aag tct    145
Ile Cys Thr Xaa Asp Phe Gln Arg Glu Pro I le Lys Pro Cys Lys Ser
            35                  40                  45 gtg tgc gag cgc gcc cgg cag ggc tgc gag c cc att ctc atc aag tac    193
Val Cys Glu Arg Ala Arg Gln Gly Cys Glu P ro Ile Leu Ile Lys Tyr
 50                  55                  60 cgc cac tcg tgg ccg gag agc cta gcc tgc g ag gag ctg ccg gta tac    241
Arg His Ser Trp Pro Glu Ser Leu Ala Cys G lu Glu Leu Pro Val Tyr
 65                  70                  75                  80 gac cgt ggt gtg tgc atc tct ccg gag gcc a tc gtc acc gct gac gga    289
Asp Arg Gly Val Cys Ile Ser Pro Glu Ala I le Val Thr Ala Asp Gly
                 85                  90                  95 gcg gac ttt cct atg gat tct agt act gga c ac tnc cgg ggg gca agc    337
Ala Asp Phe Pro Met Asp Ser Ser Thr Gly H is Xaa Arg Gly Ala Ser
            100                 105                 110 agt gaa cgc tgc aaa tgc aag cct gtc aga g cc aca cgg ang acc tng    385
Ser Glu Arg Cys Lys Cys Lys Pro Val Arg A la Thr Arg Xaa Thr Xaa
        115                 120                 125 ttc cgg aac aac tac aac tat gtg atc cgg g ct aaa gtt aaa gag gta    433
Phe Arg Asn Asn Tyr Asn Tyr Val Ile Arg A la Lys Val Lys Glu Val
    130                 135                 140 aag gca aag tgc cat gac gtg act gct gtc g tg gag gta aaa gag att    481
Lys Ala Lys Cys His Asp Val Thr Ala Val V al Glu Val Lys Glu Ile
145                 150                 155                 160 cta aag gca tct ctg gtg aac atc cca agg g at acc gtc aac ctc tac    529
Leu Lys Ala Ser Leu Val Asn Ile Pro Arg A sp Thr Val Asn Leu Tyr
                165                 170                 175 acc acc tct gga tgc ctc tgc ccc cca ctt c at gtt aat gag gaa tac    577
Thr Thr Ser Gly Cys Leu Cys Pro Pro Leu H is Val Asn Glu Glu Tyr
            180                 185                 190 atc atc atg ggt tat gaa gac gag gaa cgc t cc agg cta ctc ttg gtc    625
Ile Ile Met Gly Tyr Glu Asp Glu Glu Arg S er Arg Leu Leu Leu Val
        195                 200                 205 gag ggc acc atc gtt gag aag tgg aaa gat c gk mtt ggk rwg aar gtc    673
Glu Gly Thr Ile Val Glu Lys Trp Lys Asp X aa Xaa Xaa Xaa Xaa Val
    210                 215                 220 aag cgc tgg gat atg aaa ctt cgy cat ctt g ga ctg ggt aaa acg gat    721
Lys Arg Trp Asp Met Lys Leu Xaa His Leu G ly Leu Gly Lys Thr Asp
225                 230                 235                 240 gct agt gac tcc act cag aat cag aag gct g gc agg aac tct aat ccc    769
Ala Ser Asp Ser Thr Gln Asn Gln Lys Ala G ly Arg Asn Ser Asn Pro
                245                 250                 255 cgg cca gca gga agc t aagtcctgaa atgcgaaaga cca cacccat tgactcccct    825
Arg Pro Ala Gly Ser
            260 actaagcagt ngnatcgctg gattagcaan ggaaaatcgc attattccan t attgtttac    885 tacagatacc acgtngnatg agatgttant tctgnatcct cnccccctgn n ntctatntg    945 gcntcagtct ngntccgcaa ntctgcccat ntcgtccttc tcttccctnn t cncacaggg   1005 gnanctnctt tcttctngga ggagnngnnc ctccccncca ctattcntng t tnttccgc    1065 tcctnctttg t                                                         1076

<210> SEQ ID NO 14
<211> LENGTH: 261
<212> TYPE: PRT
<213> ORGANISM: Homo sapiens
<220> FEATURE:
<221> NAME/KEY: VARIANT
<222> LOCATION: (1)...(261)
```

-continued

<223> OTHER INFORMATION: Xaa = Any Amino Acid

<400> SEQUENCE: 14

```
Ala Asn Xaa Ile Leu Xaa Ile Xaa Gln Phe Glu Gly Leu Leu Xaa Thr
 1               5                  10                  15

His Cys Xaa Gly Asp Leu Leu Phe Phe Leu Cys Xaa Met Tyr Ala Pro
            20                  25                  30

Ile Cys Thr Xaa Asp Phe Gln Arg Glu Pro Ile Lys Pro Cys Lys Ser
        35                  40                  45

Val Cys Glu Arg Ala Arg Gln Gly Cys Glu Pro Ile Leu Ile Lys Tyr
    50                  55                  60

Arg His Ser Trp Pro Glu Ser Leu Ala Cys Glu Glu Leu Pro Val Tyr
65                  70                  75                  80

Asp Arg Gly Val Cys Ile Ser Pro Glu Ala Ile Val Thr Ala Asp Gly
                85                  90                  95

Ala Asp Phe Pro Met Asp Ser Ser Thr Gly His Xaa Arg Gly Ala Ser
            100                 105                 110

Ser Glu Arg Cys Lys Cys Lys Pro Val Arg Ala Thr Arg Xaa Thr Xaa
        115                 120                 125

Phe Arg Asn Asn Tyr Asn Tyr Val Ile Arg Ala Lys Val Lys Glu Val
130                 135                 140

Lys Ala Lys Cys His Asp Val Thr Ala Val Val Glu Val Lys Glu Ile
145                 150                 155                 160

Leu Lys Ala Ser Leu Val Asn Ile Pro Arg Asp Thr Val Asn Leu Tyr
                165                 170                 175

Thr Thr Ser Gly Cys Leu Cys Pro Pro Leu His Val Asn Glu Glu Tyr
            180                 185                 190

Ile Ile Met Gly Tyr Glu Asp Glu Glu Arg Ser Arg Leu Leu Leu Val
        195                 200                 205

Glu Gly Thr Ile Val Glu Lys Trp Lys Asp Xaa Xaa Xaa Xaa Xaa Val
    210                 215                 220

Lys Arg Trp Asp Met Lys Leu Xaa His Leu Gly Leu Gly Lys Thr Asp
225                 230                 235                 240

Ala Ser Asp Ser Thr Gln Asn Gln Lys Ala Gly Arg Asn Ser Asn Pro
                245                 250                 255

Arg Pro Ala Gly Ser
            260
```

<210> SEQ ID NO 15
<211> LENGTH: 264
<212> TYPE: PRT
<213> ORGANISM: Homo sapiens

<400> SEQUENCE: 15

```
Met Ala Arg Pro Asp Pro Ser Ala Pro Ser Leu Leu Leu Leu Leu Leu
 1               5                  10                  15

Leu Ala Gln Leu Val Gly Arg Ala Ala Ala Ala Ser Lys Ala Pro Val
            20                  25                  30

Cys Gln Glu Ile Thr Val Pro Met Cys Arg Gly Ile Gly Tyr Asn Leu
        35                  40                  45

Thr His Met Pro Asn Gln Phe Asn His Asp Thr Gln Asp Glu Ala Gly
    50                  55                  60

Leu Glu Val His Gln Phe Trp Pro Leu Val Glu Ile Gln Cys Ser Pro
65                  70                  75                  80
```

Asp Leu Arg Phe Phe Leu Cys Thr Met Tyr Thr Pro Ile Cys Leu Pro
                    85                  90                  95

Asp Tyr His Lys Pro Leu Pro Pro Cys Arg Ser Val Cys Glu Arg Ala
                100                 105                 110

Lys Ala Gly Cys Ser Pro Leu Met Arg Gln Tyr Gly Phe Ala Trp Pro
            115                 120                 125

Glu Arg Met Ser Cys Asp Arg Leu Pro Val Leu Gly Arg Asp Ala Glu
        130                 135                 140

Val Leu Cys Met Asp Tyr Asn Arg Ser Glu Ala Thr Thr Ala Pro Pro
145                 150                 155                 160

Arg Pro Phe Pro Ala Lys Pro Thr Leu Pro Gly Pro Pro Gly Ala Pro
                165                 170                 175

Ala Ser Gly Gly Glu Cys Pro Ala Gly Gly Pro Phe Val Cys Lys Cys
            180                 185                 190

Arg Glu Pro Phe Val Pro Ile Leu Lys Glu Ser His Pro Leu Tyr Asn
        195                 200                 205

Lys Val Arg Thr Gly Gln Val Pro Asn Cys Ala Val Pro Cys Tyr Gln
    210                 215                 220

Pro Ser Phe Ser Ala Asp Glu Arg Thr Phe Ala Thr Phe Trp Ile Gly
225                 230                 235                 240

Leu Trp Ser Val Leu Cys Phe Ile Ser Thr Ser Thr Thr Val Ala Thr
                245                 250                 255

Phe Leu Ile Asp Met Asp Thr Phe
            260

<210> SEQ ID NO 16
<211> LENGTH: 348
<212> TYPE: PRT
<213> ORGANISM: Homo sapiens

<400> SEQUENCE: 16

Met Arg His Asn Arg Leu Lys Val Leu Ile Leu Gly Leu Val Leu Leu
 1                5                  10                  15

Leu Thr Ser Cys Arg Ala Asp Gly Pro Leu His Ser Ala Asp His Gly
                20                  25                  30

Met Gly Gly Met Gly Met Gly Gly His Gly Leu Asp Ala Ser Pro Ala
            35                  40                  45

Pro Gly Tyr Gly Val Pro Ala Ile Pro Lys Asp Pro Asn Leu Arg Cys
        50                  55                  60

Glu Glu Ile Thr Ile Pro Met Cys Arg Gly Ile Gly Tyr Asn Met Thr
65                  70                  75                  80

Ser Phe Pro Asn Glu Met Asn His Glu Thr Gln Asp Glu Ala Gly Leu
                85                  90                  95

Glu Val His Gln Phe Trp Pro Leu Val Glu Ile Lys Cys Ser Pro Asp
                100                 105                 110

Leu Lys Phe Phe Leu Cys Ser Met Tyr Thr Pro Ile Cys Leu Glu Asp
            115                 120                 125

Tyr His Lys Pro Leu Pro Val Cys Arg Ser Val Cys Glu Arg Ala Arg
        130                 135                 140

Ser Gly Cys Ala Pro Ile Met Gln Gln Tyr Ser Phe Glu Trp Pro Glu
145                 150                 155                 160

Arg Met Ala Cys Glu His Leu Pro Leu His Gly Asp Pro Asp Asn Leu
                165                 170                 175

```
Cys Met Glu Gln Pro Ser Tyr Thr Glu Ala G ly Ser Gly Gly Ser Ser
            180                 185                 190

Gly Gly Ser Gly Gly Ser Gly Ser Gly Ser G ly Ser Gly Gly Lys Arg
        195                 200                 205

Lys Gln Gly Gly Ser Gly Ser Gly Gly Ser G ly Ala Gly Gly Ser Ser
        210                 215                 220

Gly Ser Thr Ser Thr Lys Pro Cys Arg Gly A rg Asn Ser Lys Asn Cys
225                 230                 235                 240

Gln Asn Pro Gln Gly Glu Lys Ala Ser Gly L ys Glu Cys Ser Cys Ser
            245                 250                 255

Cys Arg Ser Pro Leu Ile Phe Leu Gly Lys G lu Gln Leu Leu Gln Gln
            260                 265                 270

Gln Ser Gln Met Pro Met Met His His Pro H is His Trp Tyr Met Asn
            275                 280                 285

Leu Thr Val Gln Arg Ile Ala Gly Val Pro A sn Cys Gly Ile Pro Cys
        290                 295                 300

Lys Gly Pro Phe Phe Ser Asn Asp Glu Lys A sp Phe Ala Gly Leu Trp
305                 310                 315                 320

Ile Ala Leu Trp Ser Gly Leu Cys Phe Cys S er Thr Leu Met Thr Leu
            325                 330                 335

Thr Thr Phe Ile Ile Asp Thr Glu Arg Phe L ys Tyr
            340                 345
```

What is claimed is:

1. A method of identifying a compound that inhibits Aβ peptide levels, the method comprising:

contacting the compound with a protein selected from the group consisting of: a) Hfz5 (SEQ ID NO:4), b) Mfz4 (SEQ ID NO:6), c) Mfz7 (SEQ ID NO:8), d) Mfz7 (SEQ ID NO: 10), e) hfiz (SEQ ID NO: 12); and f) mfiz (SEQ ID NO: 14) and determining the ability of the compound to bind to the protein, wherein the binding ability of the compound is an indication that the compound lowers levels of Aβ peptide.

2. A method of identifying a compound that inhibits Aβ peptide levels, the method comprising:

(a) culturing a cell in the presence of the compound, said cell expressing a protein, and said cell producing Aβ, said protein being selected from the group consisting of: i) Hfz5 (SEQ ID NO:4), ii) Mfz4 (SEQ ID NO:6), iii) Mfz7 (SEQ ID NO:8), iv) Mfz7 (SEQ ID NO: 10), v) hfiz (SEQ ID NO:12); and vi) mfiz (SEQ ID NO:14);

(b) evaluating the level of Aβ peptide, wherein a lowered level of Aβ peptide relative to a control cell culture lacking said compound indicates the compound inhibits Aβ peptide levels.

3. A method of identifying a compound that inhibits Aβ peptide levels, the method comprising (a) contacting a cell producing detectable levels of Aβ peptide with a compound that interferes with binding between human Wnt1 and a protein selected from the group consisting of: a) Hfz5 (SEQ ID NO:4), b) Mfz4 (SEQ ID NO:6), c) Mfz7 (SEQ ID NO:8), d) Mfz7 (SEQ ID NO:10), e) hfiz (SEQ ID NO:12); and f) mfiz (SEQ ID NO:14); and (b) measuring the amount of Aβ peptide produced, wherein a decrease in the amount of Aβ peptide produced by cell in the presence of the compound indicates that the compound decreases Aβ peptide levels.

4. A method of identifying a compound that inhibits Aβ peptide levels comprising:

(a) contacting a cell producing detectable levels of Aβ peptide with a compound that binds a protein selected from the group consisting of a) Hfz5 (SEQ ID NO:4), b) Mfz4 (SEQ ID NO:6), c) Mfz7 (SEQ ID NO:8), d) Mfz7 (SEQ ID NO:10), e) hfiz (SEQ ID NO:12); and f) mfiz (SEQ ID NO:14); and (b) measuring the amount of Aβ peptide produced, wherein a decrease in the amount of Aβ peptide produced by cell in the presence of the compound indicates that the compound decreases Aβ peptide levels.

5. A method of identifying a compound that inhibits Aβ peptide levels, the method comprising:

contacting the compound with a protein and determining the ability of the compound to bind to the protein, wherein the binding ability of the compound is an indication that the compound lowers levels of Aβ peptide, said protein comprising amino acids 1–264 of SEQ ID NO:15.

* * * * *